US006368830B1

(12) United States Patent
Lampe et al.

(10) Patent No.: US 6,368,830 B1
(45) Date of Patent: Apr. 9, 2002

(54) HYPERACTIVE MUTANTS OF HIMAR1 TRANSPOSASE AND METHODS FOR USING THE SAME

(75) Inventors: David J. Lampe, Glenshaw, PA (US); Hugh M. Robertson, Urbana, IL (US); Eric J. Rubin, Waban, MA (US); Brian J. Akerley, Ann Arbor, MI (US)

(73) Assignees: President and Fellows of Harvard College, Cambridge, MA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/671,950

(22) Filed: Sep. 27, 2000

Related U.S. Application Data
(60) Provisional application No. 60/157,680, filed on Oct. 1, 1999.

(51) Int. Cl.[7] ............................ C12N 15/74; C12N 9/00; C12N 15/00; C12Q 1/37; C12P 21/04
(52) U.S. Cl. ...................... 435/69.1; 435/471; 435/183; 435/23.1; 435/70.1; 435/71.1; 435/320.1
(58) Field of Search ............................... 435/462, 320.1, 435/325, 69.1, 183, 70.1, 71.1, 471, 472; 532/23.1

(56) References Cited

FOREIGN PATENT DOCUMENTS

WO          WO 99/50402          10/1999

OTHER PUBLICATIONS

Akerley et al. (1998) "Systematic identification of essential genes by in vitro mariner mutagenesis" *Proc. Natl. Acad. Sci. USA* 95:8927–8932.
Braam et al. (1999) "A Mechanism for TN5 Inhibition" *The Journal of Biological Chemistry* 274:86–92.
Coates et al. (1998) "Mariner transposition and transformation of the yellow fever mosquito, *Aedes aegypti*" *Proc. Nation. Acad. Sci USA* 95:3748–3751.
Colloms et al. (1994) "DNA binding activities of the *Caenorhabditis elegans* Tc3 transposase" *Nucleic Acids Res.*22:5548–5554.
Craig (1995) "Unity in Transposition Reactions" *Science* 270:253–254.
Dehio and Meyer (1997) "Maintenance of Broad–Host–Range Incompatibility Group P and Group Q Plasmids and Transposition of Tn5 in *Bartonella henselae* following Conjugal Plasmid Transfer from *Escherichia coli*" *J. Bacteril.* 179:538–540.
Doak et al. (1994) "A proposed superfamily of transposase genes: Transposon–like elements in ciliated protozoa and a common "D35E" motif" *Proc. Natl. Acad. Sci. USA* 91:942–946.

Engels et al. (1987) "Somatic Effects of P Element Activity in *Drosophila melanogaster*: Pupal Lethality" *Genetics* 117:745–757.
Fadool et al. (1998) "Transposition of the mariner element from *Drosophila mauritiana* in zebrafish" *Proc. Natl. Acad. Sci. USA* 95:5182–5186.
Goryshin and Reznikoff (1998) "Tn5 in Vitro Transposition" *J. Biol. Chem.* 273:7367–7374.
Guerios–Filho and Beverley (1997) "Trans–kingdom Transposition of the Drosophila Element mariner Within the Protozoan Leishmania" *Science* 276:1716–1719.
Hartl et al. (1997) "Modern Thoughts on an Ancyent Marinere: Function, Evolution, Regulation" *Annu. Rev. Genet.* 31:337–358.
Hediger et al. (1985) "DNA sequence of the lactose operon: the lacA gene and the transcriptional termination region" *Proc. Natl. Acad. Sci. USA* 82:6414–6418.
Huisman and Kleckner (1987) "A New Generalizable Test for Detection of Mutations Affecting Tn10 Transposition" *Genetics.* 116:185–189.
Jacobson et al. (1986) "Molecular structure of a somatically unstable transposable element in Drosophila" *Proc. Natl. Acad. Sci USA* 83:8684–8688.
Johnson and Reznikoff (1984) "Role of the IS50R Proteins in the Promotion and Control of Tn5 Transposition" *J. Mol. Bio.*177:645–661.
Kennedy and Haniford (1996) "Isolation and Characterization of IS10 Transposase Separation of Function Mutants: Identification of Amino Acid Residues in Transposase that are Important for Active Site Function and the Stability of Transposition Intermediates" *J. Mol. Biol.* 256:533–547.
Krebs and Reznikoff (1988) "Use of a Tn5 derivative that creates lacZ translational fusions to obtain a transposition mutant" *Gene.* 63:277–285.
Lampe et al. (1996) "A purified mariner transpose is sufficient to mediate transposition in vitro" *EMBO J.* 15:5470–5479.

(List continued on next page.)

*Primary Examiner*—Remy Yucel
*Assistant Examiner*—Konstantina Katcheves
(74) *Attorney, Agent, or Firm*—Greenlee, Winner and Sullivan, P.C.

(57) ABSTRACT

Mariner-family transposable elements are active in a wide variety of organisms and are becoming increasingly important genetic tools in species lacking sophisticated genetics. The Himar1 element, a member of the mariner family, isolated from the horn fly, *Haematobia irritans,* is active in *Escherichia coli* when expressed appropriately. Using this fact, a genetic screen was devised to isolate hyperactive mutants of Himar1 transposase that enhance overall transposition from 4 to 50-fold as measured in an *E. coli* assay. These hyperactive Himar1 mutant transposases should enable sophisticated analysis of the biochemistry of mariner transposition and should improve efficiency of a variety of genetic manipulations involving transposition in vivo and in vitro such as random mutagenesis or transgenesis in a wide range of host cells than the transposable elements previously available.

24 Claims, 9 Drawing Sheets

OTHER PUBLICATIONS

Lampe et al. (1998) "Factors Affecting Transposition of the Himar1 mariner Transposon in Vitro" *Genetics* 149:179–187.

Lidholm et al. (1993) "The Transposable Element mariner Mediates Germline Transformation in *Drosophila melanogaster*" *Genetics* 134:859–868.

Loha and Hartl (1996) "Germline Transformation of *Drosophila virilis* With the Transposable Element mariner" *Genetics* 143:365–374.

Lohe and Hartl (1996) "Autoregulation of mariner Transposase Activity by Overproduction and Dominant–Negative Complementation" *Mol. Biol. Evol.* 13:549–555.

Lohe et al. (1995) "Horizontal Transmission, Vertical Inactivation, and Stochastic Loss of Mariner–like Transposable Elements" *Mol. Biol. Evol.* 12:62–72.

Lohe et al. (1997) "Mutations in the mariner transposase: The D,D(35)E consensus sequence is nonfunctional" *Proc. Natl. Acad. Sci. USA* 94:1293–1297.

Makris et al. (1988) "Mutational analysis of insertion sequence 50 (IS50) and transposon 5 (Tn5) ends" *Proc. Natl. Acad. Sci. USA* 85:2224–2228.

Medhora et al. (1988) "Excision of the Drosophila transposable element mariner: identification and characterization of the Mos factor" *EMBO J.* 7:2185–2189.

Reznikoff et al. (1993) "Tn5 lacZ Translation Fusion Element: Isolation and Analysis of Transposition Mutants" *Methods Enzymol.* 217:312–322.

Robertson and MacLeod (1993) "Five major subfamilies of mariner transposable elements in insects, including the Mediterranean fruit fly, and related arthropods" *Insect Molecular Biology* 2:125–139.

Robertson (1993) "The mariner transposable elements is widespread in insects" *Nature* 362:241–245.

Robertson and Asplund (1996) "Bmmar1: a Basal Lineage of the Mariner Family of Transposable Elements in the Silkworm Moth, *Bombyx mori*" *Insect Biochem. Mol. Biol.* 26:945–954.

Robertson and Lampe (1995) "Recent Horizontal Transfer of a mariner Transposable Element among and between Diptera and Neuroptera" *Mol. Biol. Eval.* 12:850–862.

Rubin et al. (1999) "In vivo Transposition of mariner–based elements in enteric bacteria and mycobacteria" *Proc. Natl. Acad. Sci. USA* 96:1645–1650.

Sherman et al. (1998) "Transposition of the Drosophila element mariner into the chicken germ line" *Nat. Biotechnol.* 16:1050–1053.

van Pouderoyen et al. (1997) "Crystal structure of the specific DNA–binding domain of Tc3 transposase of *C.elegans* in complex with transposon DNA" *EMBO J.* 16:6044–6054.

Vos et al. (1996) "Characterization of the *Caenorhabditis elegans* Tc1 transposase in vio and in vitro" *Genes Dev.* 7:1244–1253.

Weinreich et al. (1993) "A Functional Analysis of the Tn5 Transposase Identification of Domains Required for DNA Binding and Multimerization" *J. Mol. Biol.* 241:166–177.

Weinreich et al. (1994) "Evidence that the cis preference of the Tn5 transposase is caused by nonproductive multimerization" *Genes. Dev.* 8:2363–2374.

Wiegand and Reznikoff (1992) "Characterization of Two Hypertransposing Tn5 Mutants" *J. Bacteriol.* 174:1229–1239.

Zhang et al. (1998) "The Himar 1 mariner transposase cloned in a recombinant adenovirus vector is functional in mammalian cells" *Nucleic Acids Res.* 26:3687–3693.

Zhou and Reznikoff (1997) "TN5 Transposase Mutants that Alter DNA Binding Specificity" *J. Mol. Biol.* 271:362–373.

Allan R. Lohe et al. Mutations in the mariner transposase: The D,D(35)E consensus sequence is nonfunctional Proc Natl. acad Sci. USA vol. 94 pp. 1293–1297, Feb. 1997 Genetics.*

David J Lampe et al. Hyperactive transposase mutants of the Himar 1 mariner transposon Proc. Natl. Acad. Sci. USA vol. 96 pp. 11428–11433 Sep. 1999 Genetics.*

Eric J. Rubin et al. In vivo transposition of mariner–based elements in enteric bacteria and mycobacteria Proc. Natl. acad. Sci. USA vol. 96 pp. 1645–1650 Feb. 1999 Microbiology.*

Guangbin Luo et al. Chromosomal transposition of a Tc1/mariner–like element in mousde embryonic stem cells Proc. Natl. Acad. Sci. USA vol. 95 pp. 10769–10773 Sep. 1998 Genetics.*

* cited by examiner

```
                  10        20        30        40        50        60        70        80        90       100]
                   .         .         .         .         .         .         .         .         .         .]
Himar1    MEKKEFRVLIKYCFLKGKNTVEAKTWLDNEFPDSAPGKSTIIDWYAKFKRGEMSTEDGERSGRPKEVTDENIKKIHKMILNDRKMKLIEIAEALKISKE
A7        ....................................................................................................
c5        ....................................................................................................
c9        ...............................................................G....................................

110       120       130       140       150       160       170       180       190       200]
                   .         .         .         .         .         .         .         .         .         .]
Himar1    RVGHIIHQYLDMRKLCAKWVPRELTFDQKQQRVDDSERCLQLLTRNTPEFFRRYVTMDETWLHHYTPESNRQSAEWTATGEPSPKRGKTQKSAGKVMASV
A7        ..........................L.........................................................................
c5        ..................R........................................................T........................
c9        ..............K.....................................................................................

210       220       230       240       250       260       270       280       290       300]
                   .         .         .         .         .         .         .         .         .         .]
Himar1    FWDAHGIIFIDYLEKGKTINSDYYMALLERLKVEIAAKRPHMKKKKVLFHQDNAPCHKSLRTMAKIHELGFELLPHPPYSPDLAPSDFFLFSDLKRMLAG
A7        ....................................................................................................
c5        ..............................................................R.....................................
c9        ....................................................................................................

310       320       330       340]
                   .         .         .         .]
Himar1    KKFGCNEEVIAETEAYFEAKPKEYYQNGIKKLEGRYNRCIALEGNYVE
A7        ................................................
c5        ..........R.....................................
c9        ................................................
```

FIG. 8

SEQUENCE LISTING

<160> NUMBER OF SEQ ID NOS: 20

<210> SEQ ID NO 1
<211> LENGTH: 1047
<212> TYPE: DNA
<213> ORGANISM: Haematobia irritans
<220> FEATURE:

```
<221> NAME/KEY: CDS
<222> LOCATION: (1)..(1044)

<400> SEQUENCE: 1 atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
 1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
            20                  25                  30 gac tct gcc cca ggg aaa tca aca ata att gat tgg tat gca aaa ttc     144
Asp Ser Ala Pro Gly Lys Ser Thr Ile Ile Asp Trp Tyr Ala Lys Phe
        35                  40                  45 aag cgt ggt gaa atg agc acg gag gac ggt gaa cgc agt gga cgc ccg     192
Lys Arg Gly Glu Met Ser Thr Glu Asp Gly Glu Arg Ser Gly Arg Pro
    50                  55                  60 aaa gag gtg gtt acc gac gaa aac atc aaa aaa atc cac aaa atg att     240
Lys Glu Val Val Thr Asp Glu Asn Ile Lys Lys Ile His Lys Met Ile
65                  70                  75                  80 ttg aat gac cgt aaa atg aag ttg atc gag ata gca gag gcc tta aag     288
Leu Asn Asp Arg Lys Met Lys Leu Ile Glu Ile Ala Glu Ala Leu Lys
                85                  90                  95 ata tca aag gaa cgt gtt ggt cat atc att cat caa tat ttg gat atg     336
Ile Ser Lys Glu Arg Val Gly His Ile Ile His Gln Tyr Leu Asp Met
            100                 105                 110 cgg aag ctc tgt gca aaa tgg gtg ccg cgc gag ctc aca ttt gac caa     384
Arg Lys Leu Cys Ala Lys Trp Val Pro Arg Glu Leu Thr Phe Asp Gln
        115                 120                 125 aaa caa caa cgt gtt gat gat tct gag cgg tgt ttg cag ctg tta act     432
Lys Gln Gln Arg Val Asp Asp Ser Glu Arg Cys Leu Gln Leu Leu Thr
    130                 135                 140 cgt aat aca ccc gag ttt ttc cgt cga tat gtg aca atg gat gaa aca     480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg     528
Trp Leu His His Tyr Thr Pro Glu Ser Asn Arg Gln Ser Ala Glu Trp
                165                 170                 175 aca gcg acc ggt gaa ccg tct ccg aag cgt gga aag act caa aag tcc     576
Thr Ala Thr Gly Glu Pro Ser Pro Lys Arg Gly Lys Thr Gln Lys Ser
            180                 185                 190 gct ggc aaa gta atg gcc tct gtt ttt tgg gat gcg cat gga ata att     624
Ala Gly Lys Val Met Ala Ser Val Phe Trp Asp Ala His Gly Ile Ile
        195                 200                 205 ttt atc gat tat ctt gag aag gga aaa acc atc aac agt gac tat tat     672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc     720
Met Ala Leu Leu Glu Arg Leu Lys Val Glu Ile Ala Ala Lys Arg Pro
225                 230                 235                 240 cac atg aag aag aaa aaa gtg ttg ttc cac caa gac aac gca ccg tgc     768
His Met Lys Lys Lys Lys Val Leu Phe His Gln Asp Asn Ala Pro Cys
                245                 250                 255 cac aag tca ttg aga acg atg gca aaa att cat gaa ttg ggc ttc gaa     816
His Lys Ser Leu Arg Thr Met Ala Lys Ile His Glu Leu Gly Phe Glu
            260                 265                 270 ttg ctt ccc cac ccg ccg tat tct cca gat ctg gcc ccc agc gac ttt     864
Leu Leu Pro His Pro Pro Tyr Ser Pro Asp Leu Ala Pro Ser Asp Phe
        275                 280                 285 ttc ttg ttc tca gac ctc aaa agg atg ctc gca ggg aaa aaa ttt ggc     912
Phe Leu Phe Ser Asp Leu Lys Arg Met Leu Ala Gly Lys Lys Phe Gly
```

-continued

```
            290                 295                 300
tgc aat gaa gag gtg atc gcc gaa act gag gcc tat ttt gag gca aaa       960
Cys Asn Glu Glu Val Ile Ala Glu Thr Glu Ala Tyr Phe Glu Ala Lys
305                 310                 315                 320 ccg aag gag tac tac caa aat ggt atc aaa aaa ttg gaa ggt cgt tat      1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                  1047
Asn Arg Cys Ile Ala Leu Glu Gly Asn Tyr Val Glu
            340                 345

<210> SEQ ID NO 2
<211> LENGTH: 348
<212> TYPE: PRT
<213> ORGANISM: Haematobia irritans

<400> SEQUENCE: 2

Met Glu Lys Lys Glu Phe Arg Val Leu Ile Lys Tyr Cys Phe Leu Lys
  1               5                  10                  15

Gly Lys Asn Thr Val Glu Ala Lys Thr Trp Leu Asp Asn Glu Phe Pro
                 20                  25                  30

Asp Ser Ala Pro Gly Lys Ser Thr Ile Ile Asp Trp Tyr Ala Lys Phe
             35                  40                  45

Lys Arg Gly Glu Met Ser Thr Glu Asp Gly Glu Arg Ser Gly Arg Pro
 50                  55                  60

Lys Glu Val Val Thr Asp Glu Asn Ile Lys Lys Ile His Lys Met Ile
 65                  70                  75                  80

Leu Asn Asp Arg Lys Met Lys Leu Ile Glu Ile Ala Glu Ala Leu Lys
                 85                  90                  95

Ile Ser Lys Glu Arg Val Gly His Ile Ile His Gln Tyr Leu Asp Met
                100                 105                 110

Arg Lys Leu Cys Ala Lys Trp Val Pro Arg Glu Leu Thr Phe Asp Gln
             115                 120                 125

Lys Gln Gln Arg Val Asp Asp Ser Glu Arg Cys Leu Gln Leu Leu Thr
        130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
        275                 280                 285

Phe Leu Phe Ser Asp Leu Lys Arg Met Leu Ala Gly Lys Lys Phe Gly
    290                 295                 300
```

```
Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345

<210> SEQ ID NO 3
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 3 atg gaa aaa aag gaa ttt cgt gtt ttg ata aaa tac tgt ttt ctg aag     48
Met Glu Lys Lys Glu Phe Arg Val Leu Ile Lys Tyr Cys Phe Leu Lys
 1               5                  10                  15 gga aaa aat aca gtg gaa gca aaa act tgg ctt gat aat gag ttt ccg     96
Gly Lys Asn Thr Val Glu Ala Lys Thr Trp Leu Asp Asn Glu Phe Pro
            20                  25                  30 gac tct gcc cca ggg aaa tca aca ata att gat tgg tat gca aaa ttc    144
Asp Ser Ala Pro Gly Lys Ser Thr Ile Ile Asp Trp Tyr Ala Lys Phe
        35                  40                  45 aag cgt ggt gaa atg agc acg gag gac ggt gaa cgc agc gga cgc ccg    192
Lys Arg Gly Glu Met Ser Thr Glu Asp Gly Glu Arg Ser Gly Arg Pro
    50                  55                  60 aaa gag gtg gtt acc gac gaa aac atc aaa aaa atc cac aaa atg att    240
Lys Glu Val Val Thr Asp Glu Asn Ile Lys Lys Ile His Lys Met Ile
 65                 70                  75                  80 ttg aat gac cgt aaa atg aag ttg atc gag ata gca gag gcc tta aag    288
Leu Asn Asp Arg Lys Met Lys Leu Ile Glu Ile Ala Glu Ala Leu Lys
                85                  90                  95 ata tcg aag gaa cgt gtt ggt cat atc att cat caa tat ttg gat atg    336
Ile Ser Lys Glu Arg Val Gly His Ile Ile His Gln Tyr Leu Asp Met
            100                 105                 110 cgg aag ctc tgt gca aaa tgg gtg ccg cgc gag ctc aca ttt gac caa    384
Arg Lys Leu Cys Ala Lys Trp Val Pro Arg Glu Leu Thr Phe Asp Gln
        115                 120                 125 aaa caa caa cgt gtt gat gat tct gag cgg tgt ttg cag ctg tta act    432
Lys Gln Gln Arg Val Asp Asp Ser Glu Arg Cys Leu Gln Leu Leu Thr
    130                 135                 140 cgc aat aca ccc gag ttt ttc cgt cga tat gtg aca atg gat gaa aca    480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg    528
Trp Leu His His Tyr Thr Pro Glu Ser Asn Arg Gln Ser Ala Glu Trp
                165                 170                 175 acg gcg acc ggt gaa ccg tct ccg aag cgt gga aag act caa aag tcc    576
Thr Ala Thr Gly Glu Pro Ser Pro Lys Arg Gly Lys Thr Gln Lys Ser
            180                 185                 190 gct ggc aaa gta atg gcc tct gtt ttt tgg gat gcg cat gga ata att    624
Ala Gly Lys Val Met Ala Ser Val Phe Trp Asp Ala His Gly Ile Ile
        195                 200                 205 ttt atc gat tat ctt gag aag gga aaa acc atc aac agt gac tat tat    672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc    720
Met Ala Leu Leu Glu Arg Leu Lys Val Glu Ile Ala Ala Lys Arg Pro
225                 230                 235                 240
```

```
cac atg aag aag aaa aaa gtg ttg ttc cac caa gac aac gca ccg tgc       768
His Met Lys Lys Lys Lys Val Leu Phe His Gln Asp Asn Ala Pro Cys
            245                 250                 255 cac aag tca ttg aga acg atg gca aaa att cgt gaa ttg ggc ttc gaa       816
His Lys Ser Leu Arg Thr Met Ala Lys Ile Arg Glu Leu Gly Phe Glu
            260                 265                 270 ttg ctt ccc cac ccg ccg tat tct cca gat ctg gcc ccc agc gac ttt       864
Leu Leu Pro His Pro Pro Tyr Ser Pro Asp Leu Ala Pro Ser Asp Phe
            275                 280                 285 ttc ttg ttc tca gac ctc aaa agg atg ctc gca ggg aaa aaa ttt ggc       912
Phe Leu Phe Ser Asp Leu Lys Arg Met Leu Ala Gly Lys Lys Phe Gly
    290                 295                 300 tgc aat gaa gag gtg atc gcc gaa act gag gcc tat ttt gag gca aaa       960
Cys Asn Glu Glu Val Ile Ala Glu Thr Glu Ala Tyr Phe Glu Ala Lys
305                 310                 315                 320 ccg aag gag tac tac cga aat ggt atc aaa aaa ttg gaa ggt cgt tat      1008
Pro Lys Glu Tyr Tyr Arg Asn Gly Ile Lys Lys Leu Glu Gly Arg Tyr
                325                 330                 335 aat cgt tgt atc gct ctt gaa ggg aac tat gtt gaa taa                  1047
Asn Arg Cys Ile Ala Leu Glu Gly Asn Tyr Val Glu
            340                 345

<210> SEQ ID NO 4
<211> LENGTH: 348
<212> TYPE: PRT
<213> ORGANISM: Haematobia irritans

<400> SEQUENCE: 4

Met Glu Lys Lys Glu Phe Arg Val Leu Ile Lys Tyr Cys Phe Leu Lys
 1               5                  10                  15

Gly Lys Asn Thr Val Glu Ala Lys Thr Trp Leu Asp Asn Glu Phe Pro
                20                  25                  30

Asp Ser Ala Pro Gly Lys Ser Thr Ile Ile Asp Trp Tyr Ala Lys Phe
            35                  40                  45

Lys Arg Gly Glu Met Ser Thr Glu Asp Gly Arg Ser Gly Arg Pro
    50                  55                  60

Lys Glu Val Val Thr Asp Glu Asn Ile Lys Lys Ile His Lys Met Ile
65                  70                  75                  80

Leu Asn Asp Arg Lys Met Lys Leu Ile Glu Ile Ala Glu Ala Leu Lys
                85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
        115                 120                 125

Lys Gln Gln Arg Val Asp Asp Ser Glu Arg Cys Leu Gln Leu Leu Thr
    130                 135                 140

Arg Asn Thr Pro Glu Phe Phe Arg Arg Tyr Val Thr Met Asp Glu Thr
145                 150                 155                 160

Trp Leu His His Tyr Thr Pro Gly Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220
```

```
Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile Arg Glu Leu Gly Phe Glu
                260                 265                 270

Leu Leu Pro His Pro Pro Tyr Ser Pro Asp Leu Ala Pro Ser Asp Phe
            275                 280                 285

Phe Leu Phe Ser Asp Leu Lys Arg Met Leu Ala Gly Lys Lys Phe Gly
            290                 295                 300

Cys Asn Glu Glu Val Ile Ala Glu Thr Glu Ala Tyr Phe Glu Ala Lys
305                 310                 315                 320

Pro Lys Glu Tyr Tyr Arg Asn Gly Ile Lys Lys Leu Glu Gly Arg Tyr
                325                 330                 335

Asn Arg Cys Ile Ala Leu Glu Gly Asn Tyr Val Glu
                340                 345
```

<210> SEQ ID NO 5
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 5

```
atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
  1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
             20                  25                  30 gac tct gcc cca ggg aaa tca aca ata att gat tgg tat gca aaa ttc     144
Asp Ser Ala Pro Gly Lys Ser Thr Ile Ile Asp Trp Tyr Ala Lys Phe
         35                  40                  45 aag cgt ggt gaa atg agc acg gag gac ggt gaa cgc agc gga cgc ccg     192
Lys Arg Gly Glu Met Ser Thr Glu Asp Gly Glu Arg Ser Gly Arg Pro
     50                  55                  60 aaa gag gtg gtt acc gac gaa aac atc aaa aaa atc cac aaa atg att     240
Lys Glu Val Val Thr Asp Glu Asn Ile Lys Lys Ile His Lys Met Ile
 65                  70                  75                  80 ttg aat gac cgt aaa atg aag ttg atc gag ata gca gag gcc tta aag     288
Leu Asn Asp Arg Lys Met Lys Leu Ile Glu Ile Ala Glu Ala Leu Lys
                 85                  90                  95 ata tcg aag gaa cgt gtt ggt cat atc att cat caa tat ttg gat atg     336
Ile Ser Lys Glu Arg Val Gly His Ile Ile His Gln Tyr Leu Asp Met
            100                 105                 110 cgg aag ctc tgt gca aaa tgg gtg ccg cgc gag ctc aca ttt gac caa     384
Arg Lys Leu Cys Ala Lys Trp Val Pro Arg Glu Leu Thr Phe Asp Gln
        115                 120                 125 aaa caa caa cgt gtt gat gat tct gag cgg tgt ttg cag ctg tta act     432
Lys Gln Gln Arg Val Asp Asp Ser Glu Arg Cys Leu Gln Leu Leu Thr
    130                 135                 140 cgc aat aca ccc gag ttt ttc cgt cga tat gtg aca atg gat gaa aca     480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg     528
Trp Leu His His Tyr Thr Pro Glu Ser Asn Arg Gln Ser Ala Glu Trp
                165                 170                 175
```

```
acg gcg acc ggt gaa ccg tct ccg aag cgt gga aag act caa aag tcc        576
Thr Ala Thr Gly Glu Pro Ser Pro Lys Arg Gly Lys Thr Gln Lys Ser
        180                 185                 190 gct ggc aaa gta atg gcc tct gtt ttt tgg gat gcg cat gga ata att        624
Ala Gly Lys Val Met Ala Ser Val Phe Trp Asp Ala His Gly Ile Ile
    195                 200                 205 ttt atc gat tat ctt gag aag gga aaa acc atc aac agt gac tat tat        672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc        720
Met Ala Leu Leu Glu Arg Leu Lys Val Glu Ile Ala Ala Lys Arg Pro
225                 230                 235                 240 cac atg aag aag aaa aaa gtg ttg ttc cac caa gac aac gca ccg tgc        768
His Met Lys Lys Lys Lys Val Leu Phe His Gln Asp Asn Ala Pro Cys
        245                 250                 255 cac aag tca ttg aga acg atg gca aaa att cgt gaa ttg ggc ttc gaa        816
His Lys Ser Leu Arg Thr Met Ala Lys Ile Arg Glu Leu Gly Phe Glu
        260                 265                 270 ttg ctt ccc cac ccg ccg tat tct cca gat ctg gcc ccc agc gac ttt        864
Leu Leu Pro His Pro Pro Tyr Ser Pro Asp Leu Ala Pro Ser Asp Phe
    275                 280                 285 ttc ttg ttc tca gac ctc aaa agg atg ctc gca ggg aaa aaa ttt ggc        912
Phe Leu Phe Ser Asp Leu Lys Arg Met Leu Ala Gly Lys Lys Phe Gly
    290                 295                 300 tgc aat gaa gag gtg atc gcc gaa act gag gcc tat ttt gag gca aaa        960
Cys Asn Glu Glu Val Ile Ala Glu Thr Glu Ala Tyr Phe Glu Ala Lys
305                 310                 315                 320 ccg aag gag tac tac caa aat ggt atc aaa aaa ttg gaa ggt cgt tat       1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                    1047
Asn Arg Cys Ile Ala Leu Glu Gly Asn Tyr Val Glu
            340                 345

<210> SEQ ID NO 6
<211> LENGTH: 348
<212> TYPE: PRT
<213> ORGANISM: Haematobia irritans

<400> SEQUENCE: 6

Met Glu Lys Lys Glu Phe Arg Val Leu Ile Lys Tyr Cys Phe Leu Lys
  1               5                  10                  15

Gly Lys Asn Thr Val Glu Ala Lys Thr Trp Leu Asp Asn Glu Phe Pro
             20                  25                  30

Asp Ser Ala Pro Gly Lys Ser Thr Ile Ile Asp Trp Tyr Ala Lys Phe
         35                  40                  45

Lys Arg Gly Glu Met Ser Thr Glu Asp Gly Glu Arg Ser Gly Arg Pro
     50                  55                  60

Lys Glu Val Val Thr Asp Glu Asn Ile Lys Lys Ile His Lys Met Ile
 65                  70                  75                  80

Leu Asn Asp Arg Lys Met Lys Leu Ile Glu Ile Ala Glu Ala Leu Lys
                 85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
        115                 120                 125

Lys Gln Gln Arg Val Asp Asp Ser Glu Arg Cys Leu Gln Leu Leu Thr
    130                 135                 140
```

```
Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
            165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
            195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
            245                 250                 255

His Lys Ser Leu Arg Thr Met Ala Lys Ile Arg Glu Leu Gly Phe Glu
            260                 265                 270

Leu Leu Pro His Pro Pro Tyr Ser Pro Asp Leu Ala Pro Ser Asp Phe
            275                 280                 285

Phe Leu Phe Ser Asp Leu Lys Arg Met Leu Ala Gly Lys Lys Phe Gly
    290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345
```

<210> SEQ ID NO 7
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 7

```
atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
  1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
             20                  25                  30 gac tcc gcc cca ggg aaa tca aca ata att gat tgg tat gca aaa ttc     144
Asp Ser Ala Pro Gly Lys Ser Thr Ile Ile Asp Trp Tyr Ala Lys Phe
         35                  40                  45 aag cgt ggt gaa atg agc acg gag gac ggt gaa cgc agt gga cgc ccg     192
Lys Arg Gly Glu Met Ser Thr Glu Asp Gly Glu Arg Ser Gly Arg Pro
     50                  55                  60 aaa ggg gtg gtt acc gac gaa aac atc aaa aaa atc cac aaa atg att     240
Lys Gly Val Val Thr Asp Glu Asn Ile Lys Lys Ile His Lys Met Ile
 65                  70                  75                  80 ttg aat gac cgt aaa atg aag ttg atc gag ata gca gag gcc tta aag     288
Leu Asn Asp Arg Lys Met Lys Leu Ile Glu Ile Ala Glu Ala Leu Lys
                 85                  90                  95 ata tca aag gaa cgt gtt ggt cat atc att cat caa tat ttg gat atg     336
Ile Ser Lys Glu Arg Val Gly His Ile Ile His Gln Tyr Leu Asp Met
            100                 105                 110 cgg aag ctc tgt gca aaa tgg gtg ccg cgc gag ctc aca ctt gac caa     384
```

-continued

```
                Arg Lys Leu Cys Ala Lys Trp Val Pro Arg Glu Leu Thr Leu Asp Gln
                            115                 120                 125 aaa caa caa cgt gtt gat gat tct gag cgg tgt ttg cag ctg tta act         432
Lys Gln Gln Arg Val Asp Asp Ser Glu Arg Cys Leu Gln Leu Leu Thr
        130                 135                 140 cgt aat aca ccc gag ttt ttc cgt cga tat gtg aca atg gat gaa aca         480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg         528
Trp Leu His His Tyr Thr Pro Glu Ser Asn Arg Gln Ser Ala Glu Trp
                165                 170                 175 aca gcg acc ggt gaa ccg act ccg aag cgt gga aag act caa aag tcc         576
Thr Ala Thr Gly Glu Pro Thr Pro Lys Arg Gly Lys Thr Gln Lys Ser
        180                 185                 190 gct ggc aaa gta atg gcc tct gtt ttt tgg gat gcg cat gga ata att         624
Ala Gly Lys Val Met Ala Ser Val Phe Trp Asp Ala His Gly Ile Ile
                195                 200                 205 ttt atc gat tat ctt gag aag gga aaa acc atc aac agt gac tat tat         672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc         720
Met Ala Leu Leu Glu Arg Leu Lys Val Glu Ile Ala Ala Lys Arg Pro
225                 230                 235                 240 cac atg aag aag aaa aaa gtg ttg ttc cac caa gac aac gca ccg tgc         768
His Met Lys Lys Lys Lys Val Leu Phe His Gln Asp Asn Ala Pro Cys
                245                 250                 255 cac aag tca ttg aga acg atg gca aaa att cat gaa ttg ggc ttc gaa         816
His Lys Ser Leu Arg Thr Met Ala Lys Ile His Glu Leu Gly Phe Glu
                260                 265                 270 ttg ctt ccc cac ccg ccg tat tct cca gat ctg gcc ccc agc gac ttt         864
Leu Leu Pro His Pro Pro Tyr Ser Pro Asp Leu Ala Pro Ser Asp Phe
        275                 280                 285 ttc ttg ttc tca gac ctc aaa agg atg ctc gca ggg aaa aaa ttt ggc         912
Phe Leu Phe Ser Asp Leu Lys Arg Met Leu Ala Gly Lys Lys Phe Gly
    290                 295                 300 tgc aat gaa gag gtg atc gcc gaa act gag gcc tat ttt gag gca aaa         960
Cys Asn Glu Glu Val Ile Ala Glu Thr Glu Ala Tyr Phe Glu Ala Lys
305                 310                 315                 320 ccg aag gag tac tac caa aat ggt atc aaa aaa ttg gaa ggt cgt tat        1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                    1047
Asn Arg Cys Ile Ala Leu Glu Gly Asn Tyr Val Glu
                340                 345
```

<210> SEQ ID NO 8
<211> LENGTH: 348
<212> TYPE: PRT
<213> ORGANISM: Haematobia irritans

<400> SEQUENCE: 8

```
Met Glu Lys Lys Glu Phe Arg Val Leu Ile Lys Tyr Cys Phe Leu Lys
  1               5                  10                  15

Gly Lys Asn Thr Val Glu Ala Lys Thr Trp Leu Asp Asn Glu Phe Pro
            20                  25                  30

Asp Ser Ala Pro Gly Lys Ser Thr Ile Ile Asp Trp Tyr Ala Lys Phe
        35                  40                  45

Lys Arg Gly Glu Met Ser Thr Glu Asp Gly Glu Arg Ser Gly Arg Pro
    50                  55                  60
```

```
Lys Gly Val Val Thr Asp Glu Asn Ile Lys Lys Ile His Lys Met Ile
 65                  70                  75                  80

Leu Asn Asp Arg Lys Met Lys Leu Ile Glu Ile Ala Glu Ala Leu Lys
                 85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Leu Asp Gln
        115                 120                 125

Lys Gln Gln Arg Val Asp Asp Ser Glu Arg Cys Leu Gln Leu Leu Thr
    130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Thr Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
        275                 280                 285

Phe Leu Phe Ser Asp Leu Lys Arg Met Leu Ala Gly Lys Lys Phe Gly
    290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345

<210> SEQ ID NO 9
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 9 atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
  1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
             20                  25                  30 gac tct gcc cca ggg aaa tca aca ata att gat tgg tat gca aaa ttc     144
Asp Ser Ala Pro Gly Lys Ser Thr Ile Ile Asp Trp Tyr Ala Lys Phe
         35                  40                  45 aag cgt ggt gaa atg agc acg gag gac ggt gaa cgc agt gga cgc ccg     192
Lys Arg Gly Glu Met Ser Thr Glu Asp Gly Glu Arg Ser Gly Arg Pro
```

```
               50                  55                  60
aaa gag gtg gtt acc gac gaa aac atc aaa aaa atc cac aaa atg att        240
Lys Glu Val Val Thr Asp Glu Asn Ile Lys Lys Ile His Lys Met Ile
 65                  70                  75                  80 ttg aat gac cgt aaa atg aag ttg atc gag ata gca gag gcc tta aag        288
Leu Asn Asp Arg Lys Met Lys Leu Ile Glu Ile Ala Glu Ala Leu Lys
                 85                  90                  95 ata tca aag gaa cgt gtt ggt cat atc att cat caa tat ttg gat atg        336
Ile Ser Lys Glu Arg Val Gly His Ile Ile His Gln Tyr Leu Asp Met
            100                 105                 110 cgg aag ctc tgt gcg aaa tgg gtg ccg cgc gag ctc aca ttt gac caa        384
Arg Lys Leu Cys Ala Lys Trp Val Pro Arg Glu Leu Thr Phe Asp Gln
        115                 120                 125 aaa caa cga cgt gtt gat gat tct aag cgg tgt ttg cag ctg tta act        432
Lys Gln Arg Arg Val Asp Asp Ser Lys Arg Cys Leu Gln Leu Leu Thr
    130                 135                 140 cgt aat aca ccc gag ttt ttc cgt cga tat gtg aca atg gat gaa aca        480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg        528
Trp Leu His His Tyr Thr Pro Glu Ser Asn Arg Gln Ser Ala Glu Trp
                165                 170                 175 aca gcg acc ggt gaa ccg tct ccg aag cgt gga aag act caa aag tcc        576
Thr Ala Thr Gly Glu Pro Ser Pro Lys Arg Gly Lys Thr Gln Lys Ser
            180                 185                 190 gct ggc aaa gta atg gcc tct gtt ttt tgg gat gcg cat gga ata att        624
Ala Gly Lys Val Met Ala Ser Val Phe Trp Asp Ala His Gly Ile Ile
        195                 200                 205 ttt atc gat tat ctt gag aag gga aaa acc atc aac agt gac tat tat        672
Phe Ile Asp Tyr Leu Glu Lys Gly Lys Thr Ile Asn Ser Asp Tyr Tyr
    210                 215                 220 atg gcg tta ttg gag cgt ttg aag gtc gaa atc gcg gca aaa cgg ccc        720
Met Ala Leu Leu Glu Arg Leu Lys Val Glu Ile Ala Ala Lys Arg Pro
225                 230                 235                 240 cac atg aag aag aaa aaa gtg ttg ttc cac caa gac aac gca ccg tgc        768
His Met Lys Lys Lys Lys Val Leu Phe His Gln Asp Asn Ala Pro Cys
                245                 250                 255 cac aag tca ttg aga acg atg gca aaa att cat gaa ttg ggc ttc gaa        816
His Lys Ser Leu Arg Thr Met Ala Lys Ile His Glu Leu Gly Phe Glu
            260                 265                 270 ttg ctt ccc cac ccg ccg tat tct cca gat ctg gcc ccc agc gac ttt        864
Leu Leu Pro His Pro Pro Tyr Ser Pro Asp Leu Ala Pro Ser Asp Phe
        275                 280                 285 ttc ttg ttc tca gac ctc aaa agg atg ctc gca ggg aaa aaa ttt ggc        912
Phe Leu Phe Ser Asp Leu Lys Arg Met Leu Ala Gly Lys Lys Phe Gly
    290                 295                 300 tgc aat gaa gag gtg atc gcc gaa act gag gcc tat ttt gag gca aaa        960
Cys Asn Glu Glu Val Ile Ala Glu Thr Glu Ala Tyr Phe Glu Ala Lys
305                 310                 315                 320 ccg aag gag tac tac caa aat ggt atc aaa aaa ttg gaa ggt cgt tat       1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                   1047
Asn Arg Cys Ile Ala Leu Glu Gly Asn Tyr Val Glu
            340                 345

<210> SEQ ID NO 10
<211> LENGTH: 348
<212> TYPE: PRT
<213> ORGANISM: Haematobia irritans
```

```
<400> SEQUENCE: 10

Met Glu Lys Lys Glu Phe Arg Val Leu Ile Lys Tyr Cys Phe Leu Lys
 1               5                   10                  15

Gly Lys Asn Thr Val Glu Ala Lys Thr Trp Leu Asp Asn Glu Phe Pro
                 20                  25                  30

Asp Ser Ala Pro Gly Lys Ser Thr Ile Ile Asp Trp Tyr Ala Lys Phe
             35                  40                  45

Lys Arg Gly Glu Met Ser Thr Glu Asp Gly Glu Arg Ser Gly Arg Pro
         50                  55                  60

Lys Glu Val Val Thr Asp Glu Asn Ile Lys Ile His Lys Met Ile
 65                  70                  75                  80

Leu Asn Asp Arg Lys Met Lys Leu Ile Glu Ile Ala Glu Ala Leu Lys
                 85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
            115                 120                 125

Lys Gln Arg Arg Val Asp Asp Ser Lys Arg Cys Leu Gln Leu Leu Thr
        130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
        275                 280                 285

Phe Leu Phe Ser Asp Leu Lys Arg Met Leu Ala Gly Lys Lys Phe Gly
    290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345

<210> SEQ ID NO 11
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 11
```

```
atg gaa aaa aag gaa ttt cgt gtt ttg ata aaa tac tgt ttt ctg aag      48
Met Glu Lys Lys Glu Phe Arg Val Leu Ile Lys Tyr Cys Phe Leu Lys
 1               5                  10                  15 gga aaa aat aca gtg gaa gca aaa act tgg ctt gat aat gag ttt ccg      96
Gly Lys Asn Thr Val Glu Ala Lys Thr Trp Leu Asp Asn Glu Phe Pro
             20                  25                  30 gac tct gcc cca ggg aaa tca aca ata att gat tgg tat gca aaa ttc     144
Asp Ser Ala Pro Gly Lys Ser Thr Ile Ile Asp Trp Tyr Ala Lys Phe
         35                  40                  45 aag cgt ggt gaa atg agc acg gag gac ggt gaa cgc agt gga cgc ccg     192
Lys Arg Gly Glu Met Ser Thr Glu Asp Gly Glu Arg Ser Gly Arg Pro
 50                  55                  60 aaa gag gtg gtt acc gac gaa aac atc aaa aaa atc cac aaa atg att     240
Lys Glu Val Val Thr Asp Glu Asn Ile Lys Lys Ile His Lys Met Ile
 65                  70                  75                  80 ttg aat gac cgt aaa atg aag ttg atc gag ata gca gag gcc tta aag     288
Leu Asn Asp Arg Lys Met Lys Leu Ile Glu Ile Ala Glu Ala Leu Lys
                 85                  90                  95 ata tca aag gaa cgt gtt ggt cat atc att cat caa tat ttg gat atg     336
Ile Ser Lys Glu Arg Val Gly His Ile Ile His Gln Tyr Leu Asp Met
             100                 105                 110 cgg aag ctc tgt gcg aaa tgg gtg ccg cgc gag ctc aca ttt gac caa     384
Arg Lys Leu Cys Ala Lys Trp Val Pro Arg Glu Leu Thr Phe Asp Gln
         115                 120                 125 aaa caa cga cgt gtt gat gat tct gag cgg tgt ttg cag ctg tta act     432
Lys Gln Arg Arg Val Asp Asp Ser Glu Arg Cys Leu Gln Leu Leu Thr
130                 135                 140 cgt aat aca ccc gag ttt ttc cgt cga tat gtg aca atg gat gaa aca     480
Arg Asn Thr Pro Glu Phe Phe Arg Arg Tyr Val Thr Met Asp Glu Thr
145                 150                 155                 160 tgg ctc cat cac tac act cct gag tcc aat cga cag tcg gct gag tgg     528
Trp Leu His His Tyr Thr Pro Glu Ser Asn Arg Gln Ser Ala Glu Trp
                 165                 170                 175 aca gcg acc ggt gaa ccg tct ccg aag cgt gga aag act caa aag tcc     576
Thr Ala Thr Gly Glu Pro Ser Pro Lys Arg Gly Lys Thr Gln Lys Ser
             180                 185                 190 gct ggc aaa gta atg gcc tct gtt ttt tgg gat gcg cat gga ata att     624
Ala Gly Lys Val Met Ala Ser Val Phe Trp Asp Ala His Gly Ile Ile
         195                 200                 205 ttt atc gat tat ctt gag aag gga aaa acc atc aac agt gac tat tat     672
Phe Ile Asp Tyr Leu Glu Lys Gly Lys Thr Ile Asn Ser Asp Tyr Tyr
     210                 215                 220 atg gcg tta ttg gag cgt ttg aag gtc gaa atc gcg gca aaa cgg ccc     720
Met Ala Leu Leu Glu Arg Leu Lys Val Glu Ile Ala Ala Lys Arg Pro
225                 230                 235                 240 cac atg aag aag aaa aaa gtg ttg ttc cac caa gac aac gca ccg tgc     768
His Met Lys Lys Lys Lys Val Leu Phe His Gln Asp Asn Ala Pro Cys
                 245                 250                 255 cac aag tca ttg aga acg atg gca aaa att cat gaa ttg ggc ttc gaa     816
His Lys Ser Leu Arg Thr Met Ala Lys Ile His Glu Leu Gly Phe Glu
             260                 265                 270 ttg ctt ccc cac ccg ccg tat tct cca gat ctg gcc ccc agc gac ttt     864
Leu Leu Pro His Pro Pro Tyr Ser Pro Asp Leu Ala Pro Ser Asp Phe
         275                 280                 285 ttc ttg ttc tca gac ctc aaa agg atg ctc gca ggg aaa aaa ttt ggc     912
Phe Leu Phe Ser Asp Leu Lys Arg Met Leu Ala Gly Lys Lys Phe Gly
     290                 295                 300 tgc aat gaa gag gtg atc gcc gaa act gag gcc tat ttt gag gca aaa     960
Cys Asn Glu Glu Val Ile Ala Glu Thr Glu Ala Tyr Phe Glu Ala Lys
```

```
                    305                310                315                320
ccg aag gag tac tac caa aat ggt atc aaa aaa ttg gaa ggt cgt tat        1008
Pro Lys Glu Tyr Tyr Gln Asn Gly Ile Lys Lys Leu Glu Gly Arg Tyr
                325                330                335 aat cgt tgt atc gct ctt gaa ggg aac tat gtt gaa taa                    1047
Asn Arg Cys Ile Ala Leu Glu Gly Asn Tyr Val Glu
                340                345

<210> SEQ ID NO 12
<211> LENGTH: 348
<212> TYPE: PRT
<213> ORGANISM: Haematobia irritans

<400> SEQUENCE: 12

Met Glu Lys Lys Glu Phe Arg Val Leu Ile Lys Tyr Cys Phe Leu Lys
 1               5                  10                  15

Gly Lys Asn Thr Val Glu Ala Lys Thr Trp Leu Asp Asn Glu Phe Pro
            20                  25                  30

Asp Ser Ala Pro Gly Lys Ser Thr Ile Ile Asp Trp Tyr Ala Lys Phe
        35                  40                  45

Lys Arg Gly Glu Met Ser Thr Glu Asp Gly Glu Arg Ser Gly Arg Pro
    50                  55                  60

Lys Glu Val Val Thr Asp Glu Asn Ile Lys Lys Ile His Lys Met Ile
65                  70                  75                  80

Leu Asn Asp Arg Lys Met Lys Leu Ile Glu Ile Ala Glu Ala Leu Lys
                85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
        115                 120                 125

Lys Gln Arg Arg Val Asp Asp Ser Glu Arg Cys Leu Gln Leu Leu Thr
    130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255

His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
        275                 280                 285

Phe Leu Phe Ser Asp Leu Lys Arg Met Leu Ala Gly Lys Lys Phe Gly
    290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
```

325                 330                 335
Asn Arg Cys Ile Ala Leu Glu Gly Asn Tyr Val Glu
                340                 345

<210> SEQ ID NO 13
<211> LENGTH: 1047
<212> TYPE: DNA
<213> ORGANISM: Haematobia irritans
<220> FEATURE:
<221> NAME/KEY: CDS
<222> LOCATION: (1)..(1044)

<400> SEQUENCE: 13

| | | | | | | | | | | | | | | | | |
|---|---|---|---|---|---|---|---|---|---|---|---|---|---|---|---|---|
| atg | gaa | aaa | aag | gaa | ttt | cgt | gtt | ttg | ata | aaa | tac | tgt | ttt | ctg | aag | 48 |
| Met | Glu | Lys | Lys | Glu | Phe | Arg | Val | Leu | Ile | Lys | Tyr | Cys | Phe | Leu | Lys | |
| 1 | | | | 5 | | | | | 10 | | | | | 15 | | |
| gga | aaa | aat | aca | gtg | gaa | gca | aaa | act | tgg | ctt | gat | aat | gag | ttt | ccg | 96 |
| Gly | Lys | Asn | Thr | Val | Glu | Ala | Lys | Thr | Trp | Leu | Asp | Asn | Glu | Phe | Pro | |
| | | | 20 | | | | | 25 | | | | | 30 | | | |
| gac | tct | gcc | cca | ggg | aaa | tca | aca | ata | att | gat | tgg | tat | gca | aaa | ttc | 144 |
| Asp | Ser | Ala | Pro | Gly | Lys | Ser | Thr | Ile | Ile | Asp | Trp | Tyr | Ala | Lys | Phe | |
| | | 35 | | | | | 40 | | | | | 45 | | | | |
| aag | cgt | ggt | gaa | atg | agc | acg | gag | gac | ggt | gaa | cgc | agt | gga | cgc | ccg | 192 |
| Lys | Arg | Gly | Glu | Met | Ser | Thr | Glu | Asp | Gly | Glu | Arg | Ser | Gly | Arg | Pro | |
| | 50 | | | | | 55 | | | | | 60 | | | | | |
| aaa | gag | gtg | gtt | acc | gac | gaa | aac | atc | aaa | aaa | atc | cac | aaa | atg | att | 240 |
| Lys | Glu | Val | Val | Thr | Asp | Glu | Asn | Ile | Lys | Lys | Ile | His | Lys | Met | Ile | |
| 65 | | | | | 70 | | | | | 75 | | | | | 80 | |
| ttg | aat | gac | cgt | aaa | atg | aag | ttg | atc | gag | ata | gca | gag | gcc | tta | aag | 288 |
| Leu | Asn | Asp | Arg | Lys | Met | Lys | Leu | Ile | Glu | Ile | Ala | Glu | Ala | Leu | Lys | |
| | | | | 85 | | | | | 90 | | | | | 95 | | |
| ata | tca | aag | gaa | cgt | gtt | ggt | cat | atc | att | cat | caa | tat | ttg | gat | atg | 336 |
| Ile | Ser | Lys | Glu | Arg | Val | Gly | His | Ile | Ile | His | Gln | Tyr | Leu | Asp | Met | |
| | | | 100 | | | | | 105 | | | | | 110 | | | |
| cgg | aag | ctc | tgt | gcg | aaa | tgg | gtg | ccg | cgc | gag | ctc | aca | ttt | gac | caa | 384 |
| Arg | Lys | Leu | Cys | Ala | Lys | Trp | Val | Pro | Arg | Glu | Leu | Thr | Phe | Asp | Gln | |
| | | 115 | | | | | 120 | | | | | 125 | | | | |
| aaa | caa | caa | cgt | gtt | gat | gat | tct | aag | cgg | tgt | ttg | cag | ctg | tta | act | 432 |
| Lys | Gln | Gln | Arg | Val | Asp | Asp | Ser | Lys | Arg | Cys | Leu | Gln | Leu | Leu | Thr | |
| | 130 | | | | | 135 | | | | | 140 | | | | | |
| cgt | aat | aca | ccc | gag | ttt | ttc | cgt | cga | tat | gtg | aca | atg | gat | gaa | aca | 480 |
| Arg | Asn | Thr | Pro | Glu | Phe | Phe | Arg | Arg | Tyr | Val | Thr | Met | Asp | Glu | Thr | |
| 145 | | | | | 150 | | | | | 155 | | | | | 160 | |
| tgg | ctc | cat | cac | tac | act | cct | gag | tcc | aat | cga | cag | tcg | gct | gag | tgg | 528 |
| Trp | Leu | His | His | Tyr | Thr | Pro | Glu | Ser | Asn | Arg | Gln | Ser | Ala | Glu | Trp | |
| | | | | 165 | | | | | 170 | | | | | 175 | | |
| aca | gcg | acc | ggt | gaa | ccg | tct | ccg | aag | cgt | gga | aag | act | caa | aag | tcc | 576 |
| Thr | Ala | Thr | Gly | Glu | Pro | Ser | Pro | Lys | Arg | Gly | Lys | Thr | Gln | Lys | Ser | |
| | | | 180 | | | | | 185 | | | | | 190 | | | |
| gct | ggc | aaa | gta | atg | gcc | tct | gtt | ttt | tgg | gat | gcg | cat | gga | ata | att | 624 |
| Ala | Gly | Lys | Val | Met | Ala | Ser | Val | Phe | Trp | Asp | Ala | His | Gly | Ile | Ile | |
| | | 195 | | | | | 200 | | | | | 205 | | | | |
| ttt | atc | gat | tat | ctt | gag | aag | gga | aaa | acc | atc | aac | agt | gac | tat | tat | 672 |
| Phe | Ile | Asp | Tyr | Leu | Glu | Lys | Gly | Lys | Thr | Ile | Asn | Ser | Asp | Tyr | Tyr | |
| | 210 | | | | | 215 | | | | | 220 | | | | | |
| atg | gcg | tta | ttg | gag | cgt | ttg | aag | gtc | gaa | atc | gcg | gca | aaa | cgg | ccc | 720 |
| Met | Ala | Leu | Leu | Glu | Arg | Leu | Lys | Val | Glu | Ile | Ala | Ala | Lys | Arg | Pro | |
| 225 | | | | | 230 | | | | | 235 | | | | | 240 | |
| cac | atg | aag | aag | aaa | aaa | gtg | ttg | ttc | cac | caa | gac | aac | gca | ccg | tgc | 768 |
| His | Met | Lys | Lys | Lys | Lys | Val | Leu | Phe | His | Gln | Asp | Asn | Ala | Pro | Cys | |
| | | | | 245 | | | | | 250 | | | | | 255 | | |

```
cac aag tca ttg aga acg atg gca aaa att cat gaa ttg ggc ttc gaa    816
His Lys Ser Leu Arg Thr Met Ala Lys Ile His Glu Leu Gly Phe Glu
        260                 265                 270 ttg ctt ccc cac ccg ccg tat tct cca gat ctg gcc ccc agc gac ttt    864
Leu Leu Pro His Pro Pro Tyr Ser Pro Asp Leu Ala Pro Ser Asp Phe
            275                 280                 285 ttc ttg ttc tca gac ctc aaa agg atg ctc gca ggg aaa aaa ttt ggc    912
Phe Leu Phe Ser Asp Leu Lys Arg Met Leu Ala Gly Lys Lys Phe Gly
        290                 295                 300 tgc aat gaa gag gtg atc gcc gaa act gag gcc tat ttt gag gca aaa    960
Cys Asn Glu Glu Val Ile Ala Glu Thr Glu Ala Tyr Phe Glu Ala Lys
305                 310                 315                 320 ccg aag gag tac tac caa aat ggt atc aaa aaa ttg gaa ggt cgt tat   1008
Pro Lys Glu Tyr Tyr Gln Asn Gly Ile Lys Lys Leu Glu Gly Arg Tyr
                325                 330                 335 aat cgt tgt atc gct ctt gaa ggg aac tat gtt gaa taa                1047
Asn Arg Cys Ile Ala Leu Glu Gly Asn Tyr Val Glu
            340                 345

<210> SEQ ID NO 14
<211> LENGTH: 348
<212> TYPE: PRT
<213> ORGANISM: Haematobia irritans

<400> SEQUENCE: 14

Met Glu Lys Lys Glu Phe Arg Val Leu Ile Lys Tyr Cys Phe Leu Lys
 1               5                  10                  15

Gly Lys Asn Thr Val Glu Ala Lys Thr Trp Leu Asp Asn Glu Phe Pro
            20                  25                  30

Asp Ser Ala Pro Gly Lys Ser Thr Ile Ile Asp Trp Tyr Ala Lys Phe
        35                  40                  45

Lys Arg Gly Glu Met Ser Thr Glu Asp Gly Arg Ser Gly Arg Pro
    50                  55                  60

Lys Glu Val Val Thr Asp Glu Asn Ile Lys Lys Ile His Lys Met Ile
65                  70                  75                  80

Leu Asn Asp Arg Lys Met Lys Leu Ile Glu Ile Ala Glu Ala Leu Lys
                85                  90                  95

Ile Ser Lys Glu Arg Val Gly His Ile Ile His Gln Tyr Leu Asp Met
            100                 105                 110

Arg Lys Leu Cys Ala Lys Trp Val Pro Arg Glu Leu Thr Phe Asp Gln
        115                 120                 125

Lys Gln Gln Arg Val Asp Asp Ser Lys Arg Cys Leu Gln Leu Leu Thr
    130                 135                 140

Arg Asn Thr Pro Glu Phe Phe Arg Arg Tyr Val Thr Met Asp Glu Thr
145                 150                 155                 160

Trp Leu His His Tyr Thr Pro Glu Ser Asn Arg Gln Ser Ala Glu Trp
                165                 170                 175

Thr Ala Thr Gly Glu Pro Ser Pro Lys Arg Gly Lys Thr Gln Lys Ser
            180                 185                 190

Ala Gly Lys Val Met Ala Ser Val Phe Trp Asp Ala His Gly Ile Ile
        195                 200                 205

Phe Ile Asp Tyr Leu Glu Lys Gly Lys Thr Ile Asn Ser Asp Tyr Tyr
    210                 215                 220

Met Ala Leu Leu Glu Arg Leu Lys Val Glu Ile Ala Ala Lys Arg Pro
225                 230                 235                 240

His Met Lys Lys Lys Val Leu Phe His Gln Asp Asn Ala Pro Cys
                245                 250                 255
```

```
                245                 250                 255
His Lys Ser Leu Arg Thr Met Ala Lys Ile His Glu Leu Gly Phe Glu
            260                 265                 270

Leu Leu Pro His Pro Pro Tyr Ser Pro Asp Leu Ala Pro Ser Asp Phe
            275                 280                 285

Phe Leu Phe Ser Asp Leu Lys Arg Met Leu Ala Gly Lys Lys Phe Gly
        290                 295                 300

Cys Asn Glu Glu Val Ile Ala Glu Thr Glu Ala Tyr Phe Glu Ala Lys
305                 310                 315                 320

Pro Lys Glu Tyr Tyr Gln Asn Gly Ile Lys Lys Leu Glu Gly Arg Tyr
                325                 330                 335

Asn Arg Cys Ile Ala Leu Glu Gly Asn Tyr Val Glu
            340                 345

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
cccctcgagc catggaaaaa aaggaatttc gtg                                 33

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
ccgctcagaa tcatcaacac gtt                                            23

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
tacccgggaa tcatttgaag gttggtac                                       28

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
taatacgact cactataggg                                                20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
```

-continued

```
      Oligonucleotide primer

<400> SEQUENCE: 19
aacgaatttt aacaaaaaaa tgtg                                        24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
cgatttaggt gacactatag                                             20
```

HYPERACTIVE MUTANTS OF HIMAR1 TRANSPOSASE AND METHODS FOR USING THE SAME

CROSS REFERENCE TO RELATED APPLICATIONS

This application claims priority from U.S. Provisional Application Serial No.60/157,680, filed Oct. 1, 1999.

ACKNOWLEDGMENT OF FEDERAL RESEARCH SUPPORT

This invention was made, at least in part, with funding from the United States Department of Agriculture (USDA 95-37302-1796), the Public Health Service and the National Institutes of Health (AI33586-01). Accordingly, the United States Government may have certain rights in this invention.

BACKGROUND OF THE INVENTION

The field of this invention is the area of molecular genetics, in particular, in the area of mobile genetic elements, e.g., transposons, the transposase enzymes responsible for mobility and methods for isolating mutant transposase enzymes which mediate higher frequencies of transposition than do the naturally occurring enzymes, and uses thereof.

Transposable genetic elements are DNA sequences, found in a wide variety of prokaryotic and eukaryotic organisms, that can move or transpose from one position to another position in a genome. In vivo, intra-chromosomal transpositions as well as transpositions between chromosomal and non-chromosomal genetic material are well known. In several systems, transposition is known to be under the control of a transposase enzyme that is typically encoded by the transposable element. The genetic structures and transposition mechanisms of various transposable elements are summarized, for example, in "Transposable Genetic Elements" in "The Encyclopedia of Molecular Biology," Kendrew and Lawrence, Eds., Blackwell Science, Ltd., Oxford (1994).

Mariner-family transposable elements are a diverse and taxonomically widespread group of transposons occurring throughout the animal kingdom [Robertson, (1993) Nature 362:241–245; Robertson and MacLeod, (1993) Insect Mol. Biol. 2:125–139; Robertson and Asplund, (1996) Insect Biochem. Mol. Biol. 26:945–954; Robertson, et al. (1998) Horizontal Gene Transfer, eds. Syvanen and Kado (Chapman & Hall, London)]. They encode transposases that belong to an extended superfamily of transposases and retroviral integrases distinguished by a conserved D,D35E (or variants thereof mariners=D,D34D) motif in the catalytic domain of the protein [Doak, et al. (1994) Proc. Natl. Acad. Sci. USA 91:842–946]. Transposition of these elements follows a conservative cut-and-paste mechanism [Craig, (1995) Science 270:253–254].

Most mariners are known only from their sequences obtained either through homology-based PCR screens or by the examination of sequenced genes or ESTs [Roberts (1993) supra; Robertson and Lampe, (1995) Mol. Biol. Eval. 12:850–862]. Hundreds of different mariners have been detected in this way. Of these, only two are known to be active. The first is the canonical mariner element from Drosophila mauritiana discovered by its activity in that fly [Jacobson, et al. (1986) Proc. Natl. Acad. Sci. USA. 83:8684–8688]. The most active copy of this particular element is known as MosI [Medhorn, et al. (1988) EMBO J. 7:2185–2189]. The second is the Himar1 element discovered by using homology-based PCR in the horn fly, Hacmatobia irritans, and reconstructed as a consensus sequence [Robertson, et al. (1986) supra; Lampe, et al. (1996) EMBO J. 15:5470–5479]. Both MosI and Himar1 require no host-specific factors for transposition and so have been advanced as generalized genetic tools [Loha and Hartl, (1996) Genetics 143:3265–374; Gueiros-Filho and Beverley, (1997) Science 276:1716–1719; Lampe, et al. (1998) Genetics 149:179–187]. Indeed, MosI has been used as a transformation vector for chicken [Sherman, et al. (1998) Nat. Biotechnol. 16:1050–1053], zebrafish [Fadool, et al. (1998) Proc. Natl. Acad. Sci. USA 95:5182–5186], the yellow fever mosquito, Aedes Aegypri [Coates, et al. (1998) Proc. Nation. Acad. Sci. USA 95:3748–3751], Drosophila melanogaster [Lidholm, et al. (1993) Genetics 134:859–868], Drosophila virilis [Loha and Hartl (1996) supra], and Leishmanla major [Guiros-Filho, (1997) supra], with varying degrees of success. Himar1 has been used as a prokaryotic genetic tool, via in vivo transposition and subsequent homologous recombination in Haemophilus influenzae and Streptococcus pneumoniae, and in vivo in Escherichia coli and Mycobacterial spp. [Akerley, et al. (1998) Proc. Natl. Acad. Sci. USA 95:8927–8932; Rubin, et al. (1999) Proc. Natl. Acad. Sci. USA 96:1645–1650]. It is also active in human cells [Zhang, et al. (1998) Nucleic Acids Res. 26:3687–3693].

Whereas mariner elements are becoming increasingly important tools for eukaryotic genetics, neither MosI nor Himar1 appear to be as active as would be desired to make them efficient tools, particularly for whole metazoa [Lampe, et al. (1998) supra; Fadool (1998) supra]. In fact, these transposases may have evolved to be less active in their hosts and, therefore, be less deleterious [Lampe, et al. (1998) supra; Lohe and Hartl, (1996) Mol. Biol. Eval. 13:549–555; Hartl, (1997) Genetics 100:177,184]. Such low transposition activity makes the use of these elements for genetic manipulations less practical. Identifying mutant transposases with higher activity might help to solve this problem but is difficult to carry out in metazoan systems [Lohe, et al. (1997) Proc. Natl. Acad. Sci. USA 94:1293–1297].

In order to identify mutant transposases with higher activity and a broad host range, the ability of Himar1 to transpose in prokaryotes was exploited to create a genetic system for isolation of transposase mutants with altered activity in vitro and in vivo. The present invention discloses three highly active mutants that significantly improve the efficiency of transposition of Himar1-derived elements as genetic tools. Analysis of these mutants shows the locations of functional domains and amino acids within the Himar1 transposase. The hyperactive mutants of Himar1 transposase described herein are useful in generating random mutations in vivo and in vitro or in introducing a heterologous DNA into a wide range of host cells.

SUMMARY OF THE INVENTION

The present invention provides mutant Himar1 mariner transposase proteins and coding sequences therefor. These mutant transposases are such that the frequency of transposition is significantly higher than the comparison transposase which occurs in nature. By significantly higher, it is meant at least about 2-fold higher, and desirably greater than about 5-fold, and including the ranges of about 3 to about 1000-fold, and all ranges therebetween. The mutant transposases of the present invention further exhibit the useful property of being active in a wide range of prokaryotic and eukaryotic cells, including but not limited to bacteria, insects, nematodes, flatworms, and vetebrates (e.g. humans). Thus, these mutant transposases can be used to improve the efficiency of a variety of genetic manipulations which require the step of transposition of a genetic element.

The mutant Himar1 tranposases of the invention were identified as having higher transposition efficiency by a combination of the trans-papillation screen and the mating assay. The mutant transposases of the invention represent the first example of the eukaryotic transposases isolated using these assays. Using the combination of these two assays, additional transposase mutants with a varying transposition frequency can be isolated from the Himar1 transposon or any related transposable elements.

The hyperactive mutant transposases of the present invention are useful in a variety of genetic manipulations which require a transposition event in vitro and in vivo. These include but are not limited to sequencing of unknown DNA, generating random mutations in vitro or in vivo such as gene knock-outs, introducing a gene of interest, or identification of essential genes in an organism.

The hyperactive Himar1 transposase mutant proteins can be expressed and purified for use in in vitro assays using the methods known in the art. The nucleic acid coding sequences for the mutant transposases provided herein can be cloned into a transposon such as Himar1 to be used for in vivo transposition.

BRIEF DESCRIPTION OF THE DRAWINGS

FIG. 6A shows strategy for producing chromosomal mutations by using in vitro transposon mutagenesis. FIG. 6B shows genetic footprinting for detection of essential genes.

FIG. 8 is the amino acid sequence alignment of the wild type Himar1 transposase protein (SEQ ID NO:2) and three hyperactive mutant proteins described in the Specification as A7, C5 and C9 (SEQ ID NOs. 4, 8, and 10 respectively). The amino acid residues that are identical in all four proteins are indicated as dots in the mutant proteins.

DETAILED DESCRIPTION OF THE INVENTION

Figure 1:
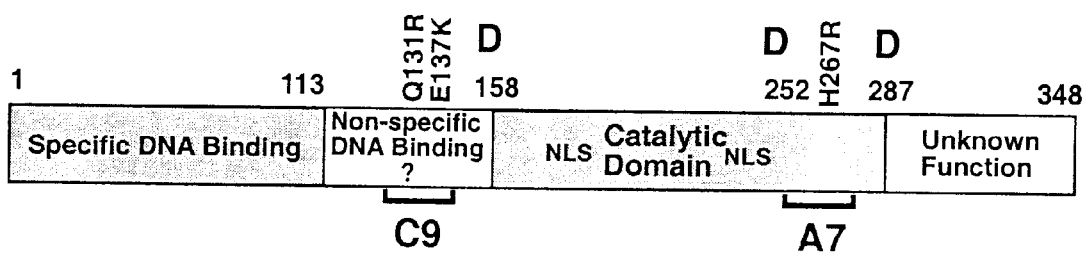
FIG. 1 is a schematic diagram of Himar1 transposase showing notable landmarks, proposed functional domains, and the positions of the hyperactive mutations described herein. The putative DNA-binding domains are based on comparisons to the Tc1 and Tc3 transposases of *C. elegans* and to computer predictions of Tc1/mariner transposase structures. "D" indicates the positions of the catalytic residues of the putative D,D34D catalytic domain. Specific amino acids noted are hyperactive mutations described in the invention. C9 and A7 refer to clones for those specific mutants as described in the Specification. NLS refers to the positions of two putative nuclear localization signals (beginning at positions 184 and 243, respectively) as predicted by the program PSORT [Nakai and Kanchisa (1992) *Genomics* 14:897–911].

The following definitions are provided to remove any ambiguities as to intent or scope of their usage in the specifications and claims.

A "wild type Himar1 transposase" is intended to mean a transposase which occurs in nature and contains the amino acid sequence as given in SEQ ID NO:2. This transposase is used as control to compare the transposition frequency of the mutant transposases of the invention. A "mutant" Himar1 transposase refers to a transposase which is different from the wild type transposase in one or more amino acid residues as exemplified herein. The mutant Himar1 transposases can be generated by point mutations, substition, deletion, or insertion mutations and identified as having a higher transposition frequency than the control transposase employing the assays disclosed herein. The present invention discloses six mutant Himar1 transposases which exhibit a transposition frequency at least about-two fold higher than the control transposase in the mating-out assay described herein. The transposition frequency of a mutant Himar1 transposase can also be measured in any art-recognized assay such as an in vitro transposition assay or a mating-out assay as described in the present invention along with a control transposase. Of the six mutants, the A7 (SEQ ID NOs:3 and 4) and C9 (SEQ ID NOs:9 and 10) mutants contain two amino acid changes as shown in FIG. 8 and four mutants named C5, E1, B1 and B2 contain single amino acid substitutions as follows: C5 (E66G, SEQ ID NOs:7 and 8), E1(H267R, SEQ ID NOs:5 and 6), B1(Q131R, SEQ ID NOs:11 ans 12) and B2(E137K, SEQ ID NOs:13 and 14). Synonymous codings are within the scope of the present invention, and are well within the grasp of the ordinary skilled artisan without the expense of undue experimentation, given the teachings of the present disclosure taken with what is well known in the art.

"A host" or "host cell" as used herein refers to an organism, cell or tissue which serves as target or recipient for transposable elements to insert themselves into. A host cell or host can also indicate a cell or host which expresses a recombinant protein of interest when the host cell is transformed with an expression vector containing a gene of interest.

The term "vector" refers to a nucleic acid molecule capable of transporting another nucleic acid molecule to which it has been linked. One type of vector is a plasmid vector which often contains a coding sequence for a selectable marker (e.g. antibiotic resistance gene). Certain vectors are capable of directing the expression of a gene to which they are operably linked. Such vectors are referred to herein as "expression vectors".

The "expression vectors" of the invention comprise a nucleic acid encoding a mutated transposase of Himar1 operably linked for expression of the nucleic acid in a host cell, which means that the vectors include one or more regulatory sequences, selected on the basis of the host cells to be used in a manner suitable for expression. The term, "regulatory sequences" is intended to include promoters, enhancers, transcription termination signals, polyadenylation sequences, and other expression control elements.

The term, "transformation" or "transfection" refers to a method of introducing DNA into a host cell. Transformation or transfection can be carried out by various methods known in the art including electroporation, calcium-phosphate precipitation, protoplast fusion etc.

"Primer" refers to a single stranded deoxynucleic acid molecule of at least about 10 nucleotides in length up to generally about 25 nucleotides in length.

The present invention is based on the discovery that certain mutants of the Himar1 mariner transposases exhibit an increased frequency of transposition in vitro compared to that of wild type Himar1 transposase. Because of the wide host range of the Himar1 transposons and the fact that no host factors are required for transposition to occur, the mutants described herein are useful as genetic tools in a variety of methods which require a transposition event in vitro and in vivo.

Figure 2A:
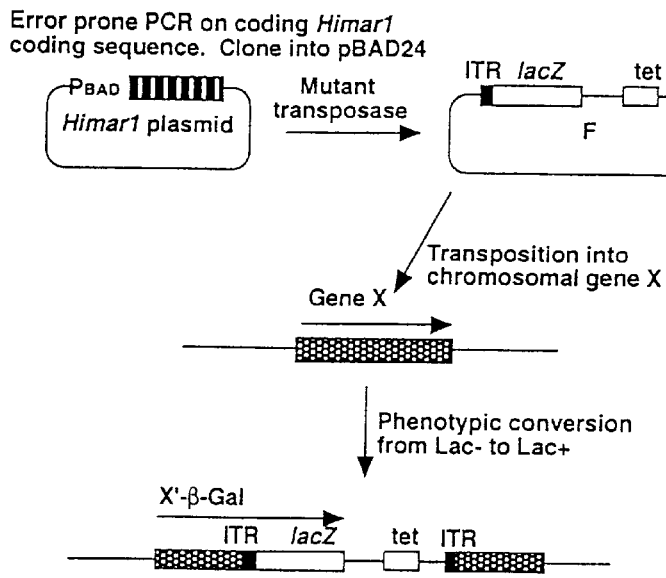
FIG. 2A is a papillation assay used for detection of mutant Himar1 transposases. The papillation screen was used to examine a pool of mutant transposase sequences to isolate hyperactive transposases.

To introduce a mutation in the coding region of the Himar1 transposase, error-prone PCR was employed to create a pool of transposase mutants as shown in FIG. 2A. A papillation screen was used to detect altered levels of transposition frequency. The Himar1 papillation screen is based on the ability of Himar1 to mobilize a nonautonomous Himar1 transposon carrying an in-frame fusion of a lazZ gene off an F plasmid and into the *E. coli* chromasome. If the transposon insertion fuses in frame with an expressed *E. coli* gene, a protein fusion can be produced that contains β-gal activity. The Lac(+) subpopularion of cells in an otherwise Lac(−) *E. coli* colony can metabolize lactose if plated on MacConkey agar. The Lac(+) cells grow faster than the surrounding Lac(−) cells and thus will produce bumps, or papillae, on the colony. Moreover, these paillae turn red on MacConkey lactose agar because of the production of lactic acid and its detection by the neutral red in the media. The greater the number of papillae produced after a given period of time, the greater is the frequency of transposition.

Transposition of Himar1 in *E. coli* was readily detected by using the papillation screen. Papillation only occurred when using Himar1 transposase constructs. The proportion of colonies showing any transpositional activity depended strongly on the concentration of $MnCl_2$ used in the error-prone PCR. Using 250 µM $MnCl_2$, we recovered only one hypertransposer (A7) among 2,500 colonies screened, the vast majority of which were nulls or hypomorphs, presumably through introduction of multiple mutations. Using 100 µM $MnCl_2$, the number of colonies showing papillation of some degree to ≈30% was increased and 10 potential hypertransposers were recovered from 2,300 colonies screened.

Figure 2B:
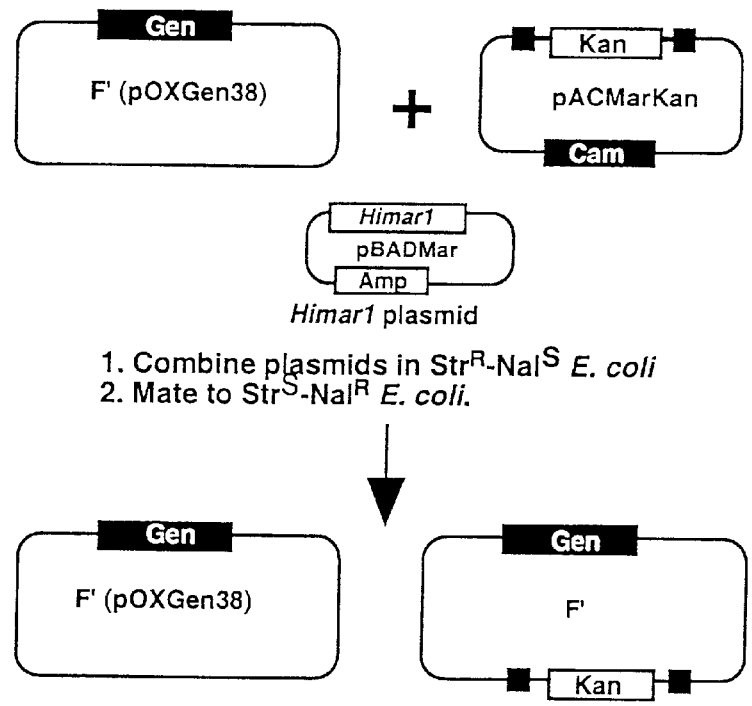
FIG. 2B shows a mating-out assay used for measuring transposition frequency of mutant Himar1 transposases. This assay quantifies the relative frequency of individual transposase constructs.

A mating-out assay was used to measure quantitatively the relative frequency of transposition produced by individual transposases [Huisman and Kleckner, (1987) supra; Johnson and Reznikoff, (1984) *J. Mol. Biol.* 177:645–661]. This assay measures the frequency with which an F plasmid is used as a target by a nonautonomous Himar1 transposon mobilized by a given transposase source. After mating the target F plasmids to a recipient strain, the transposition frequency is determined by measuring the ratio of F plasmids carrying KanR (the marker in Himar1) to all exconjugates (FIG. 2B).

Figure 3:
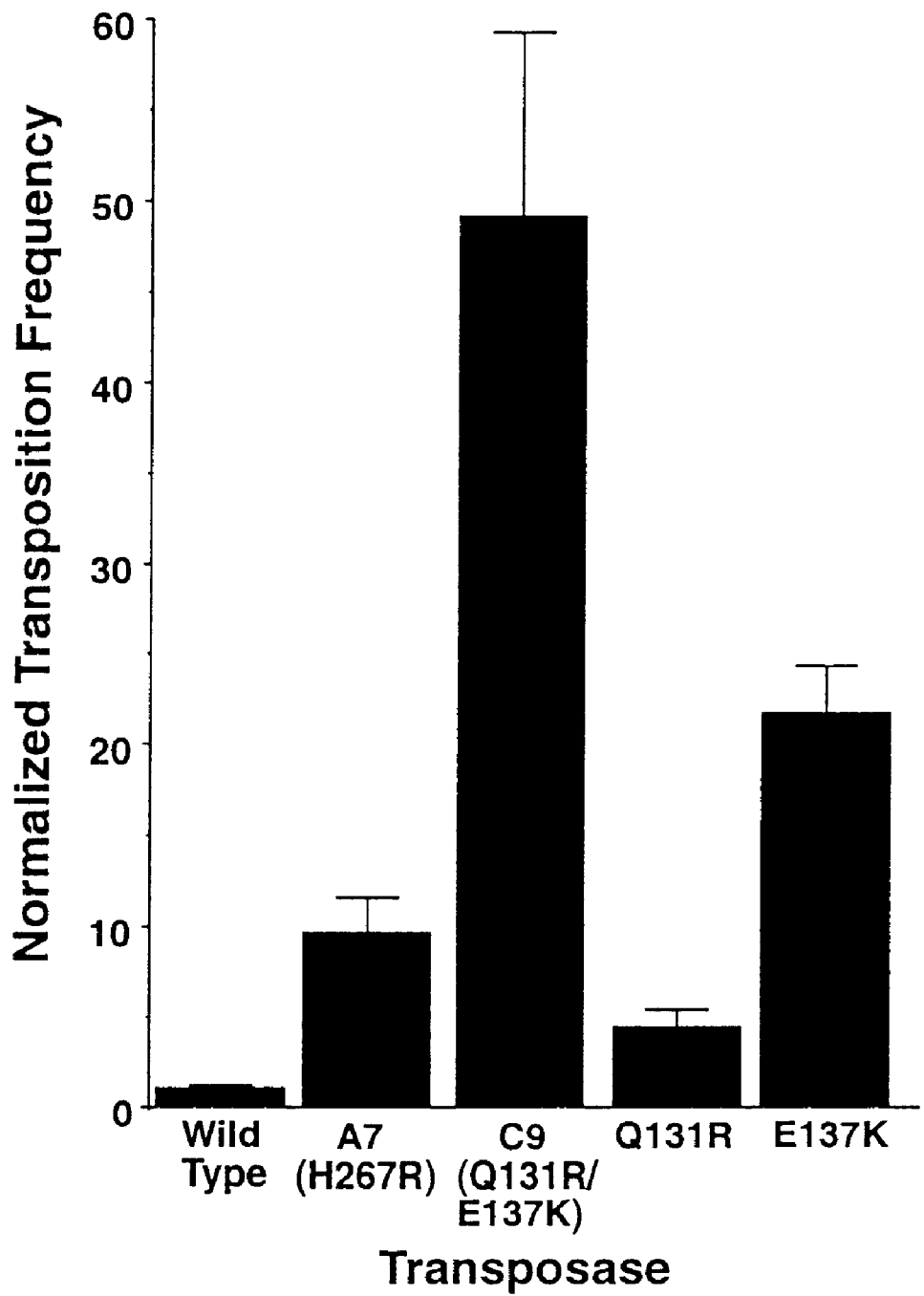
FIG. 3 shows relative activity of wild-type and hyperactive Himar1 transposases as measured in the mating-out assay. The frequency of transposition is expressed relative to that of wild-type Himar1 transposase which has been normalized to a value of 1.0. A typical transposition frequency for wild-type transposase under the conditions described here is ~$4\times10^{-6}$. Relative frequencies are calculated by dividing each of the absolute frequencies by the average absolute transposition frequency of wild-type Himar1 transposase. The errors are SEM. Relative errors are computed by dividing the absolute errors by the mean absolute frequency for the wild-type transposase.

Two mutants, named A7 and C9, were particularly active in the papillation screen and so were chosen for further analysis in the mating-out assay. The A7 mutant was ≈10-fold more active in *E. coli* than the wild type whereas the C9 mutant was ≈50-fold more active (FIG. 3). Sequencing showed that both mutants contained multiple amino acid changes (two each in A7 and C9). By substituting wild-type sequences for mutated ones and testing the isolated mutant amino acid changes again in the papillation assay, it was possible to determine which amino acid changes actually conferred the hyperactivity. Doing this, it was found that a H267R change in mutant A7 (this mutant is renamed as E1) and both the Q131R and E137K changes in mutant C9 conferred hyperactivity (FIG. 1). Testing the individual C9 mutations in the mating-out assay showed that the Q131R mutation alone (this mutant is named B1) was ≈4-fold more hyperactive whereas the E137K alone (this mutant is named B2) was ≈20-fold more hyperactive. The combination of these mutations is ≈50-fold more active, indicating that these mutations act synergistically, and not simply additively.

Most of the seemingly hyperactive mutants isolated in the papillation assay were not hyperactive in the mating-out assay. The reason for this is unclear, but false positive results have been reported in similar assays with both Tn10 and Tn5 [Huisman and Kleckner (1987) supra; Krebs and Raznikoff (1988) supra]. Wild-type Himar1 is most active at 30° C. [Lampe, et al. (1998) supra], so the fact that the mutants were isolated at 32° C. and their activity was measured at 37° C. indicates that A7 and C9 are more stable at the higher temperature used for the mating-out assay.

To examine whether the hyperactive mutations described above were attributable to some novel interaction with the *E.*

Figure 4A:
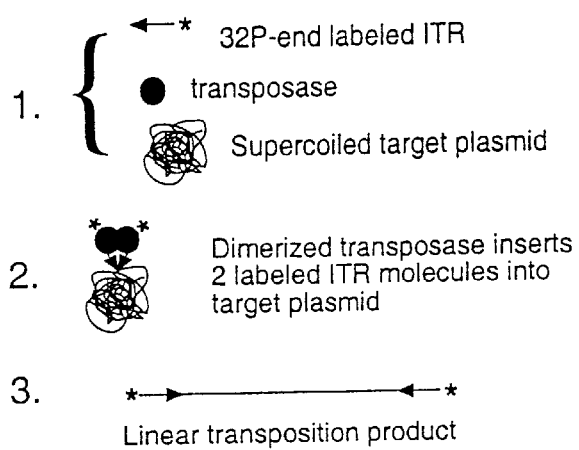
FIG. 4A is an overview of in vitro transposition assay. Purified transposase is mixed with a short $^{32}$P-end-labeled DNA fragment containing the 5' ITR of Himar1 and cold supercoiled plasmid target DNA. Transposition using two labeled ITR fragments is equivalent to a normal transposition event by Himar1. The target DNA was linearized and labeled with $^{32}$P, which is easily measured by autoradiography and phosphorimaging. The rate at which the product accumulates is a measure of the transposition frequency.
Figure 4B:
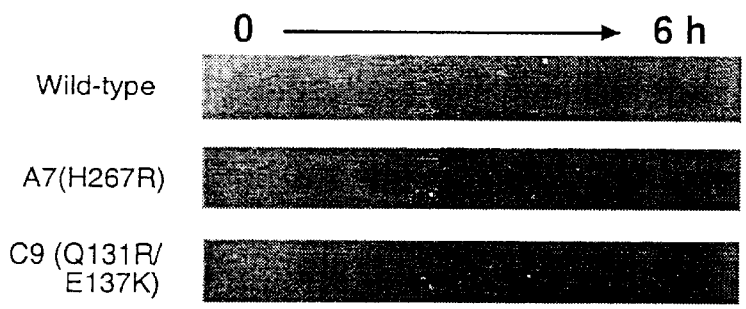
FIG. 4B shows typical results of the in vitro assay. Autoradiograph showing the accumulation of the radiolabeled linear transposition product for wild-type, E1 (H267R), and C9 (Q131]R/E137K) transposases, respectively, over a period of 6 h.
Figure 4C:
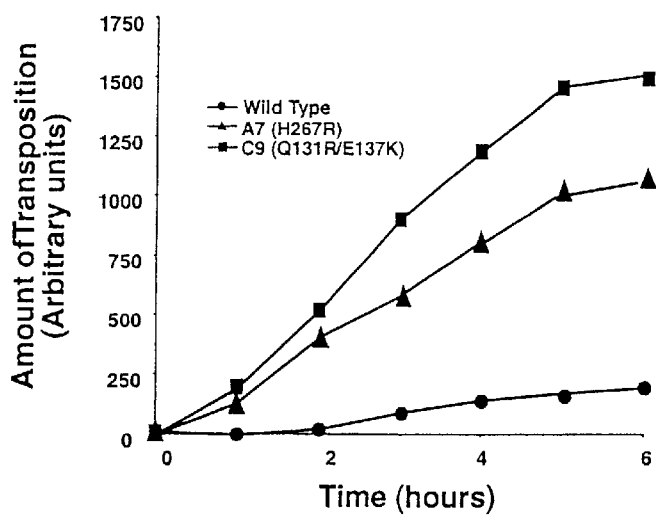
FIG. 4C is a graphical representation of the data in FIG. 4B. The gel was analyzed by using a Molecular Dynamics PhosphorImager. The values on the y axis are density units based on the numbers of pixels per unit area as measured by IMAGEQUANT software.
Figure 5:
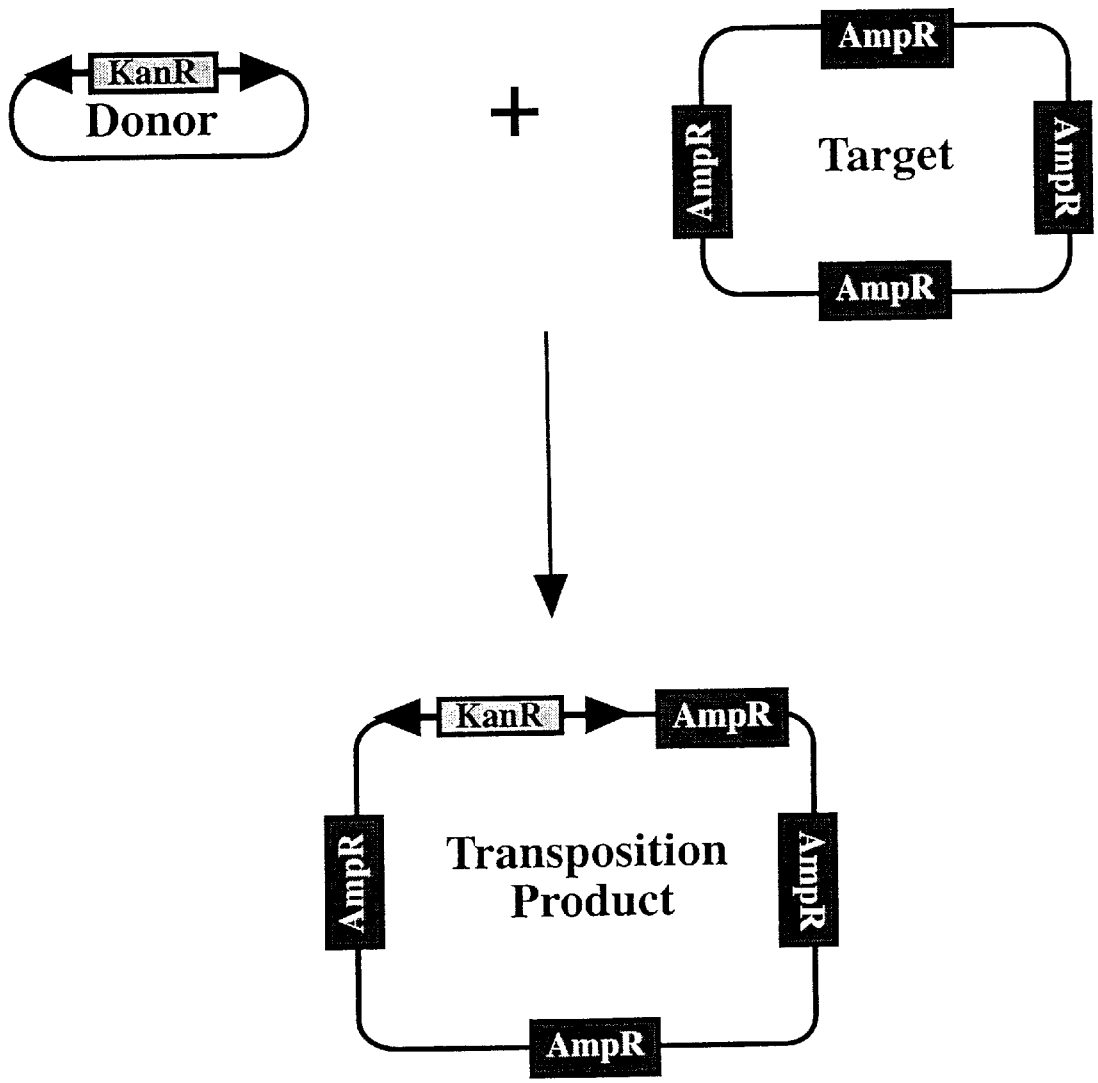
FIG. 5 illustrates an overview of the method to create random insertions into purified DNA using a mutant Himar1 transposase of the invention in vitro. The details of this assay can be found in Example 9. Briefly, in vitro transposition assay is initiated by adding purified transposase to a mixture of donor and target plasmids. After incubating at room temperature for 2 hrs, the DNA is extracted and transformed into *E. coli*. The transformed bacterial cells are then plated on LB-ampicillin agar plates to test for DNA recovery and on LB-ampicillin/kanamycin agar-plates to detect transposition products. The transposition frequency is scored by dividing the number of colonies that are resistant to ampicillin and kanamycin with the number of colonies that are resistant to ampicillin alone. The transposition products can also be sequenced or subjected to restriction analysis to confirm their identity.

*coli* host and not to some property in the transposase itself, purified E1 and C9 transposases were tested in an in vitro transposition assay. This assay measured the relative ability of purified transposase to process and insert two $^{32}$P end-labeled ITR DNA fragments into an unlabeled supercoiled DNA target, thus producing a labeled linear transposition product that is easily quantified (FIG. 4A). The rate at which this labeled product accumulates is a measure of transposition frequency. FIGS. 4B and 4C show that the E1 and C9 transposases were both hyperactive compared with the wild type. By measuring the slopes of the linear portions of the curves in FIG. 4C (between 1 and 5 h), one can compare the rate of product accumulation. By this analysis, the A7 transposase was 4.8-fold more active than the wild type whereas C9 was 7-fold more active. Thus, the purified transposases were less active in the in vitro assay than in the mating-out assay. These results, however, do confirm that hyperactivity is intrinsic to the transposase protein and not the result of some novel interaction with *E. coli*.

In vitro mutagenesis is rapidly becoming an important tool for studies of gene function. The Himar1 mariner system has been used to mutagenize targeted genomic regions of the chromosome of a human respiratory pathogen, *Haemophilus influenzae* [Akerly, et al. (1998) supra]. Analysis of such regions is enhanced by using large pools of mutants, which requires high efficiency of transposition. This system was used to test whether the hyperactive transposases could improve mutagenesis frequencies. Wild-type, A7, and C9 transposases were tested for the ability to move the minimariner element Tn-magellan1 carrying the gene for kanamycin resistance into a PCR-amplified chromosomal segment of *H. influenzae*. After repair of single-strand gaps introduced into the target DNA by the transposition reaction, DNA was transformed into competent *H. influenzae* cultures as described [Akerly, et al. (1998) supra]. The number of Kan-resistant *H. influenzae* colonies obtained with the wild-type, A7, and C9 transposases were 217±122, 633±50, and 733±49, respectively. These results indicate that mutagenesis of *H. influenzae* with Himar1 is significantly improved by the use of hyperactive transposases of the present invention.

Mariner transposons are well known for their wide distribution in animals, which suggests that they do not rely on any host-specific factors for transposition. Indeed, members of the Tcl-mariner1 superfamily are active in a wide range of organisms, and both Tcl and Himar1 transposases are capable of catalyzing transposition in the absence of any host proteins [Lampe, et al. (1996) supra; Vos, et al. (1996) *Genes Dev.* 7:1244–1253. The recent finding that Himar1 is active in *E. Coli* [Rubin, et al. (1999) supra] has provided the opportunity to utilize bacterial genetic methods to create and study transposase mutants of this eukaryotic transposon in a manner that would be very difficult in a metazoan system. Mutants of MosI mariner have been isolated by ethane methyl-sulfonate (EMS) mutagenesis in *Drosophila melanogaster*, but this system is laborious, and only mutations that negatively affected transposition were detected [Lohe, et al. (1997) supra]. The combination of the papillation screen and mating-out assay in *E. Coli* described above is a simple method to produce mutants of mariners and any other related transposases and ascertain their level of activity.

Two hyperactive mutants (A7 and C9) disclosed herein are double mutants. The fact that both amino acid changes in C9 mutant contributed synergistically to the overall hyperactivity in a quantitative mating assay suggests that additional combinations of mutants constructed directly, or by shuffling during the mutagenesis, might be even more hyperactive.

Although there is no structural data available for the Himar1 transposase, analysis of the mutant sequence along with comparison to other known transposases suggests the locations of functional domains. The only structural information for any of the Tcl-mariner superfamily of transposons is that for the *Caenorhabditis elegans* transposase Tc3, and then only for the specific DNA binding domain, a region that does not include the Himar1 mutations [van Pouderoyen, et al. (1997) *EMBO J.* 16:6044–6054]. Functional studies have been performed for both Tcl and Tc3 transposases that demonstrated the existence of a separate, nonspecific DNA binding domain in each [Vos, et al. (1993) *Genes Dev.* 7:1244–1253; Colloms, et al. (1994) *Nucleic Acids Res.* 22:5548–5554]. By comparing Tcl and Tc3 transposases and computer models [Pietrokovski and Henikoff (1997) *Mol. Gen. Gener.* 254:689–695] with Himar1 transposase, specific DNA binding is likely to be encoded by the first approximately 113 amino acids of Himar1, nonspecific DNA binding by approximately amino acids 114–173, and catalysis by at least amino acids 158–287, the first and last amino acids of the D, D34D catalytic triad (FIG. 1). The C-terminal-most region is of unknown function. Given the fact that the Q131R and E137K mutations occur in a region of the transposase implicated in nonspecific DNA binding, the enhanced activity in these mutants may be attributable to increased affinity for DNA in general (FIG. 1). Similarly, the H267R mutation, which occurs in the putative catalytic domain, may be attributable to increased or altered catalysis. In Tn5 transposase, these various regions are known to overlap extensively, so a mutation in one region may affect a completely different property of the transposase [Braam, et al. (1999) *J. Biol. Chem.* 274:86–92]. Indeed, the ways in which a transposase can be hyperactive are diverse. For example, at least three different classes of hyperactive mutations have been uncovered for Tn5. These affect the production of cotranslated inhibitor protein [Wiegand and Reznikoff (1992) *J. Bacteriol.* 174:1229–1239], an increase in the affinity of Tn5 transposase for ITR DNA [Zhou and Reznikoff (1997) *J. Mol. Biol.* 271:362–373], and a decrease in the self-inhibitory activity of intact Tn5 transposase [Weinreich, et al. (1994) *Genes. Dev.* 8:2363–2374]. The combination of these three classes of hyperactive mutants are synergistic, leading to an extraordinarily active transposase [Goryshin and Reznikoff, (1998) *J. Biol. Chem.* 273:7367–7374].

Abundant sequence information is available for members of the Tcl-mariner family of transposons. Alignment of the available transposase sequences [Robertson and Asplund (1996) supra] allowed us to determine whether any of the amino acid replacements identified in the Himar1 hyperactive mutants are present in related transposases. Interestingly, one of the amino acid changes is present in a homologous position in the highly active Mos1 mariner. This transposase contains an arginine residue at the position of the Q131R mutation. This is not a highly conserved position in mariner transposases generally, although Tcl-like elements are biased toward basic residues at this position. The E137R mutation is not present in most other mariner family elements because this region is a unique small insertion in the irritans subfamily of mariner transposases to which Himar1 belongs. Finally, the H267R replacement of A7 is shared with one other member of the irritans subfamily (Hsmar2) and two members of the mellifera subfamily (Gpmar1) and Demar1), but again, this is not a widely conserved position in mariner transposases.

Reznikoff and coworkers have stressed that the ability to isolate hyperactive transposases of Tn5 strongly suggests it has not evolved for maximal activity [Braam, et al. (1999) supra]. Tn5 transpsase mutants have been isolated that can increase the intrinsic activity of the transposase or eliminate regulatory mechanisms [Zhou and Reznikoff (1997) supra; Weinreich, et al. (1994) *Annu. Rev. Genet.* 241:166–177]. Low intrinsic activity and self-regulation appear to allow Tn5 to persist in *E. Coli* without producing serious levels of genetic damage. The fact that hyperactive mutants for Himar1 were isolated may be attributable to similar evolutionary forces at work on mariner-family transposons. Horizontal transfer is a major feature in the evolutionary history of these mobile genes [Robertson, et al. (1998) supra; Robertson and Lampe (1995) supra; Hartl, et al. (1997) *Annu. Rev. Genet.* 31:337–358; Lohe, et al. (1995) *Mol. Biol. Evol.* 12:62–72]. Clearly, the elements must be active enough to make copies of themselves when they transfer to a new host to persist. If not, they will be eliminated because of stochastic mechanisms [Lohe, et al. (1995) supra]. Their activity, however, cannot be so high as to significantly reduce the fitness of the host. Unregulated transposition can be highly deleterious to a host organism [Engels, et al. (1987) *Genetics* 117:745–757]. Thus, the mariners that persist in nature are not likely to be present in their most active forms. From the standpoint of copy number in the host organism, Himar1 is very successful, being present in 17,000 copies of the *H. irritans* genome [Robertson and Lampe (1995) supra]. It may be that this success is attributable to a fairly benign level of activity in that genome because of either a comparatively low intrinsic activity level, some self-regulatory mechanism [Lampe, et al. (1998) supra], or both. The fact that hyperactive forms of the Himar1 transposases were isolated as disclosed herein is consistent with this view.

The primary advantage of the Himar1 mutants disclosed herein is that they make Himar1 transposition more efficient both in vivo and in vitro. For applications such as in vitro mutagenesis for identifying essential genes in an organism as described in Akerley et al. (1998) supra, one can complete the project with much less starting material and obtain higher total numbers of desired mutants while avoiding the inherent difficulty of scaling up existing procedures. In cases where one wishes to use the transposon to mark genes in vivo, many fewer events need to be screened and in some cases the increase in transposition efficiency will allow detection of mutations which were too infrequent to be detected using previously available technology. For applications such as DNA sequencing, use of a highly efficient transposon such as hyperactive Himar1 transposase should make creation of sequencing templates quicker and easier than using existing transposases.

Hyperactive Himar1 mutants of the invention are particularly useful in creating random insertions at high frequency into purified DNA in vitro. One application for doing this is to introduce "islands" of known sequence (e.g. transposase) into unknown DNA so that the unknown DNA can be sequenced using primers derived from the known sequence. Another application of the insertions made in vitro is to knock out a gene of interest in vivo by homologous recombination if the insertion introduced in vitro is directed to the region of a gene of interest. There are kits commercially available for generating random insertions based on the primer island concept ("Primer Island Transposition Kit", Applied Biosystems, The Perkin-Elmer Corporation, Foster City, Calif. and "Genome Priming System", New England Biolabs, Inc.). However, the Himar1 transposases of the present invention provide higher transposition efficiency and broader host range than any system currently available. In vitro gene knock-outs can also be generated using this method depending on the location of the random Himar1 insertion in a given target DNA. The details of the methodology for introducing random Himar1 insertions into a plasmid is described in Lampe, et al. (1996) supra.

The Himar1 tranposons containing hyperactive mutant transposase can be used to generate mutants in a living organism by in vivo transposition. This is analogous to the in vitro transposition method described above except the living organism is used under controlled conditions to mobilize the transposon into random location in the genome. For this, a specific phenotypic screen needs to be designed which will allow the detection of a particular class of mutants of a given gene. The principle behind this application is outlined in FIG. 7.

All of the utilities of the hyperactive Himar1 transposases described above can be practiced in a wide variety of prokaryotic and eukaryotic cells including humans. This eliminates the need for having to isolate endogenous transposases from an experimental system as has been the case previously.

Figure 7:
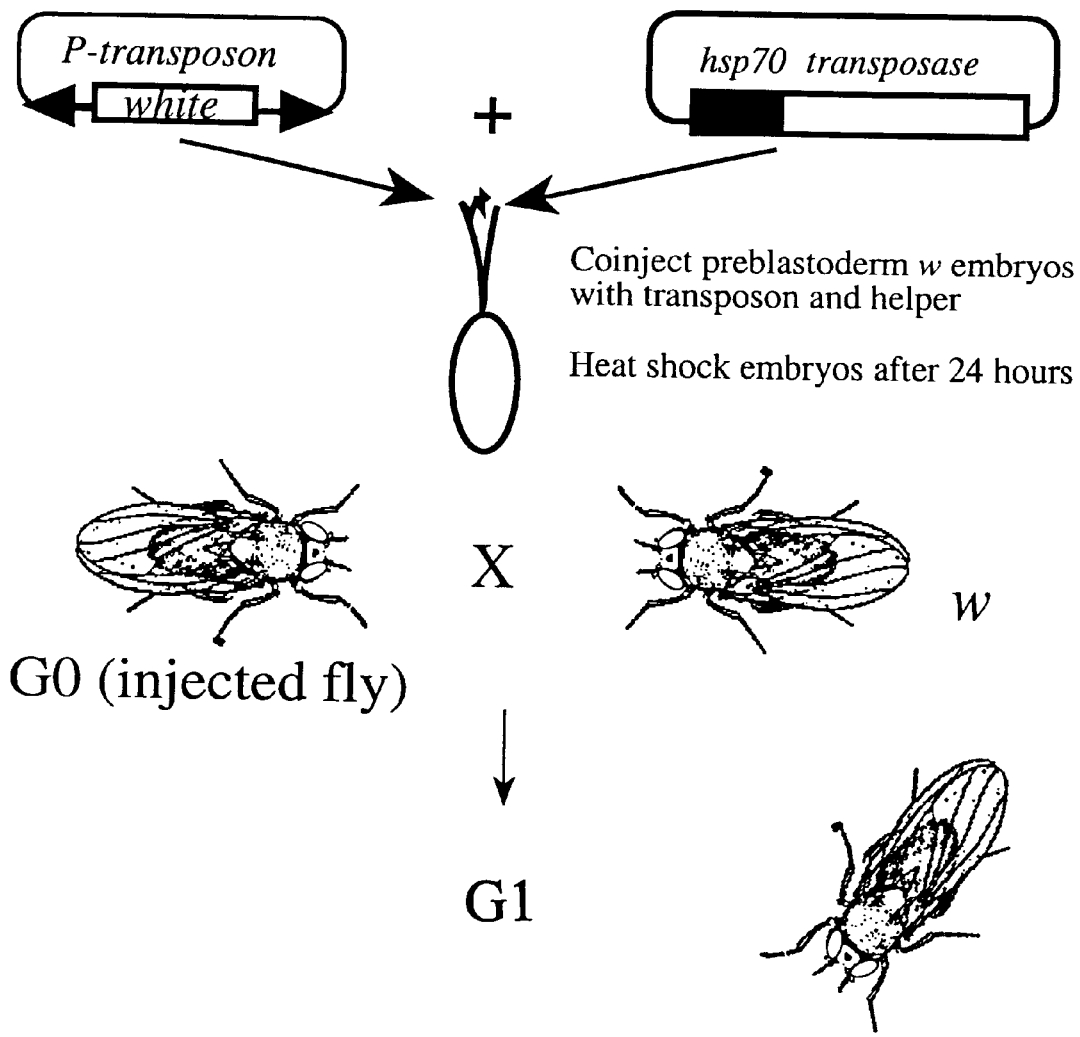
FIG. 7 illustrates a typical scheme for using the P-element to transform *D. melanogaster*. All other proposed methods of transforming *D. melanogaster* using transposons are derivatives of this scheme. The presence of red eyes in G1 progeny indicates transposition of the P-element from the injected plasmid into the germline chromosomes which can be inherited by the progeny of the injected fly.

Another utility of the Himar1 transposases of the invention lies in generating transgenes in vivo by introducing exogenous DNA into the germline of a target organism in a controlled manner, generally in single copy. The principle of this can be illustrated using the P element transposon of Drosophila as shown in FIG. 7. Two plasmids are injected into preblastoderm embryos in the area of the presumptive germ line. One plasmid carries the transposon construct having P element terminal sequences flanking the heterologous DNA to be inserted and the other is a transposase gene lacking the DNA sequences for mobility. Tranposase produced by transcription and translation off the transposase gene construct can mobilize the modified P element off its plasmid and integrate it into the chromosome. The Himar1 transposons containing the hyperactive mutants of the present invention can be used similarly in cell culture for both eukaryotic and prokaryotic cells.

Hyperactive transposase mutants such as those described here can be used and are well suited for both in vivo and in vitro work. For in vitro applications, purified mutant protein is needed. The nucleic acids encoding three hyperactive mutants of Himar1 transposase are provided in the present specification. Therefore, one skilled in the art can readily clone the nucleic acid for a given mutant transposase into an expression vector and produce recombinant Himar1 transposase using methods described herein in combination with the techniques well known in the art. For in vivo applications, the mutant protein can be expressed in vivo from a transposon such as Himar1 comprising the nucleic acid encoding a mutant transposase. The two mutants of the invention are somewhat tolerant of high temperatures, which would be particularly useful in *E. Coli* and human cells. Another application of the hyperactive mutants is in functional genomic analysis to identify essential genes in an organism. A method known as GAMBIT [Akerly, et al. (1998) supra] has been used for this purpose, however, using the hyperactive mutant transposases disclosed herein will make the method more efficient. Particularly labor-intensive methods such as germline transformation could be eased by more active transposases, such as those disclosed in the present invention.

TABLE 1

Bacterial strains and plasmids used in the present invention

| Strains, plasmids | Description |
| --- | --- |
| Strains | |
| β2155 | thrB1004 pro thi strA hsdS lacZΔM15 (F' lacZΔM15 lacI9 traD36 proA + proB +) ΔdapA::erm (=EmR) pir:RP4 [::kan (KmR) from SM10] |
| HB101 | supE44 hsdS20 ($r_B$-$m_B$-) recA13 ara-14 proA2 acY1 galK2 rpsL20 xyl-5 mtl-1 |
| HBfLac | HB101 F::miniHimar1 LacTet from pMMLacTet |
| DH5α | Δ(lac)U169 endA1 gyrA96 hsdR17 recA1 relA1 supE44 thi-1 φ80lacZΔM15 |
| DL1 | DH5α F::miniHimar1LacTet from pMMLacTet |
| RZ212/pOX38-Gen | D(lac-pro), ara, str recA56, srl, thi, |
| RZ212MK | RZ212/ pACMarKan (mating-out strain) |
| RZ221 | polA, Δ(lac-pro), ara, str nal |
| BL21(DE3) | F-, omp T, $r_B$-$m_B$- \| DE3 |
| Plasmids | |
| pMMOrf | Like pMMar but with ORF througth 3' ITR |
| pMMLacTet | pMMOrf containing lacZYA and Tet$^r$ gene |
| pBCMAR | Himar1 coding sequence under $P_{lac}$ control |
| pMarNco | Himar1 coding sequence with NcoI at start site |
| pRZ1495 | Tn5 papillation factor |
| p27fH-5' | pK19 containing left (5') ITR of Himar1 |
| pACMarKan | pACYC184 carrying Kan$^r$ Himar1 |
| pMarNde18 | Himar1 lacking ITR sequences |
| pMinimariner | Himar1 of only the first and last 100 bp |
| pBAD24 | Expression plasmid with ara$_{BAD}$ promoter |
| pBADMar1 | Himar1 tpase under ara$_{BAD}$ promoter |
| pBADH267R | As pBADMar1 but with H267R mutation |
| pBADC9 | As pBADMar1 but with Q131R and E137K mutations in Himar1 tpase |
| pET29A7 | pET29b+ carrying H267R mutation in Himar1 tpase |
| pET29C9 | pET29b+ carrying Q131R and E137K mutations in Himar1 tpase |
| pCDNAII | Target plasmid for in vitro reactions |

Techniques and agents for introducing and selecting for the presence of heterologous DNA in animal cells, insect cells, yeast cells, bacterial cells, plant cells and/or tissue are well-known. Genetic markers allowing for the selection of heterologous DNA in plant and other eukaryotic cells are well-known, e.g., genes carrying resistance to an antibiotic such as kanamycin, hygromycin, gentamicin, or bleomycin. The marker allows for selection of successfully transformed cells growing in the medium containing the appropriate antibiotic because they will carry the corresponding resistance gene. Selective markers for bacterial cells are also well known, and include those resistant to kanamycin, ampicillin, tetracycline, chloramphenicol, mercuric ion, among others. The skilled artisan can readily select an appropriate selective marker for a particular cell or strain and a particular vector and/or resistance gene.

Techniques for genetically engineering animal, insect, yeast, plant or bacterial cells and/or tissue to contain and express a transposase of the present invention are well known to the art, and the choice of a method for introducing heterologous DNA depends on the cell to be so modified. Techniques include Agrobacterium-mediated transformation, electroporation, microinjection, particle bombardment, transformation, transfection or other techniques known to the art.

Many of the procedures useful for practicing the present invention, whether or not described herein detail, are well known to those skilled in the art of molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook, et al. (1989) *Molecular Cloning,* Second Edition, Cold Spring Harbor Laboratory, Plainview, N.Y.; Maniatis, et al. (1982) *Molecular Cloning,* Cold Spring Harbor Laboratory, Plainview, N.Y.; Wu (ed.) (1993) *Meth. Enzymol.* 218: Part I; Wu (ed) (1979) *Meth Enzymol* 68; Wu, et al. (eds) (1983) *Meth. Enzymol.* 100 and 101; Grossman and Modave (eds.) *Meth. Enzymol.* 65: Miller (ed.) (1972) *Experiments in Molecular Genetics,* Cold Spring Harbor Laboratory, Cold Spring Harbor, N.Y.; Old and Primrose (1981) *Principles of Gene Manipulation* University of California Press, Berkeley; Schleif and Wensink (1982) *Practical Methods in Molecular Biology;* Glover (ed.) (1985) *DA Cloning* Vol. I and II, IRL Press, UK; Hames and Higgins (eds.) (1985) *Nucleic Acid Hybridization,* IRL Press, Oxford, UK; and Setldow and Hollaender (1979) *Genetic Engineering: Principles and Methods,* Vols. 1–4, Plenum Press, New York, Kaufman (1987) in *Genetics Engineering Principles and Methods,* J. K. Setlow, ed., Plenum Press, NY, pp. 155–198; Fitchen, et al. (1993) *Annu. Rev. Microbiol.* 47:739–764; Tolstoshev, et al. (1993) in *Genomic Research in Molecular Medicine and Virology,* Academic Press. Abbreviations and nomenclature, where employed, are deemed standard in the field and commonly used in professional journals such as those cited herein.

All references cited in the present application are incorporated by reference herein to the extent that they are not inconsistent with the present disclosure.

EXAMPLES

The following examples are provided for illustrative purposes, and are not intended to limit the scope of the invention as claimed herein. Any variations in the exemplified articles which occur to the skilled artisan are intended to fall within the scope of the present invention.

Example 1

Media and Antibiotics

Strains were grown at the temperatures indicated in LB broth or on agar plates prepared as described [Sambrook, et al. (1989) *Molecular Cloning A Laboratory Manual* (Cold Spring Harbor Lab. Press, Plainview, N.Y.)]. Papillation assays were performed on thick McConkey lactose agar plates. Antibiotics concentrations were ampicillin (Amp), 100 μg; gentamicin (Gen), 10 μg; kanamycin (Kan), 40 μg; tetracycline (Tet), 34 μg; naladixic acid (Nal), 20 μg; chloramphenicol (Cam), 34 μg, all per ml, respectively, except where otherwise noted.

Example 2

Plasmids and Bacterial Strains pMarNco was constructed via PCR using the primers 5'-CCCCTCGAGCCATGGAAAAAAAGGAATTTCGTG-3' (SEQ ID NO:15) and 5'-CCGCTCAG-AATCATCAACACGTT-3' (SEQ ID NO:16) and pMarNde18 [Lampe, et al. (1996) supra] as a template. The resulting PCR fragment and pMarNde18 were cut with XhoI and EcoRV and were ligated to created pMarNco, which contains the Himar1 transposase coding sequence with an NcoI site at the start codon. pBCMar was constructed by cleaving pMarNde18 with PstI, creating a blunt end using T4 DNA polymerase, then digesting with XhoI. The fragment that encodes the transposase was gel purified and cloned into pBCKS+ that had been digested with XhoI and Ecl1361.

A miniHimar1 transposon containing an ORF through the 3' inverted terminal repeat (ITR) was constructed by PCR using a PCR-ligation-PCR method [Ali and Steinkasserer, (1995) BioTechniques18:746–750]. The 5' ITR was amplified with primers 5' TACCCGGGAATCATTTGAAGGT-TGGTAC (76rSma, SEQ ID NO:17) and 5' TAATACGACT-CACTATAGGG (T7, SEQ ID NO:18), and the 3' ITR was amplified with the primers 5'AACGAATTTTAA-CAAAAAAATGTG (Mar3'r, SEQ ID NO:19) and 5'CGATTTAGGTGACACTATAG (SP6, SEQ ID NO:20), both using pMinimariner [Lampe, et al. (19989) supra] as a template and Pfu polymerase. The two separate PCR reactions were treated with T4 polynucleotide kinase and ATP. Five microliters of each kinase reaction were ligated with T4 DNA ligase for 15 min at room temperature. Another PCR reaction then was performed by using the SP6 and T7 primers and 1 µl of the ligation as a template, using Taq DNA polymerase. The resulting product was cloned as a t-tailed fragment into a pTAdv1 (CLONETECH, Palo Alto, Calif.), producing pTAdvMMOrf. This clone was cut with BamHI, and the fragment containing the minimariner was isolated and ligated to the BamHI site of pCDNAII (Invitrogen, Carlsbad, Calif.) to produced pMMOrf which contains a unique BglII site in the middle of the element.

A papillation construct was produced by cleaving pMMOrf with BglII and ligating it to the BamHI/BglII fragment of pRZ1495 [Makris, et al. (1998) Proc. Natl. Acad. Sci. USA 85:2224–2228] to produce pMMLacTet. The lacZ gene of this insert has no transcriptional or translational controls [Hediger, et al. (1985) Proc. Natl. Acad. Sci. USA 82:6414–6418].

An F-plasmid containing the papillation transposon from pMMLacTet was produced by transforming E. Coli β2155 [Dehlo and Meyer (1997) J. Bacteriol. 179:538–540] by electroporation with pMCMar and pMMLacTet with selection on Amp, Cam (20 µg/ml), and diaminopimelic acid. Diaminopimelic acid is required for growth of β2155, which is a dapA mutant. Approximately 5,000 colonies were pooled and mixed with HB101 for a 6 h of mating on LB agar. Exconjugants in which the F' from β2155 was mated out into HB101 were selected on Tet and Xgal (20 µg/ml) in the absence of diaminopimelic acid, resulting in colonies that were dark blue, light blue, white, or mosaic. White colonies were picked and colony purified on a second LB-Tet-Xgal plate. Resulting clones were patched to plates containing either Amp, Cam, Kan, or Tet, and clones confirmed to be $Amp^s$, $Cam^s$, $Kan^s$, and $Tet^R$ were named HBFlac.

To verify that the HBFlac strains contain functional Himar1'lacZ elements, they were transformed with pBCMar and were selected on Cam and Xgal. The resulting colonies were dark blue, light blue, white and mixed (i.e., exhibited blue papillae on white colonies). The F' from HBFlac3 (the lightest blue strain) was transferred to DH5α by conjugation with selection on Nal and Tet, yielding the strain DL1.

A Himar1 transposon for use in the mating-out assay was constructed by ligating the BamHI/EagI fragment of pMar-Kan [Lampe, et al. (1996) supra] containing a KanR-marked Himar1 transposon to the BamHI/EagI fragment of pACYC184, resulting in the plasmid pACMarKan.

E. Coli protein expression plasmids were made for each of the hyperactive transposase mutants by cutting the pBAD24 vectors containing the hyperactive inserts with NcoI, making this site blunt with Klenow, and cutting again with KpnI. The coding sequence fragments were purified from a 0.5% 1×TAE (40 mM Tris-acetate/1 mM EDTA) gel and were ligated to the NdeI (made blunt with Klenow as above)/KpnI sites of pET29b+ (Novagen, Madison, Wis.), yielding pET29A7 and pET29C9 for the pBADA7- and pBADC9-containing transposase mutants, respectively. A vector capable of expressing C5 mutant protein can be prepared similarly.

Example 3

Transposase Mutagenesis

Mutations were introduced into the coding region of Himar1 transposase by error-prone PCR using pMarNco as a template [Zhou and Reznikoff (1997) J. Mol. Biol. 271:362–373]. The reactions contained ≈2 ng of template DNA, 50 mM KCl, 10 mM Tris HCl (pH 9.0 at 25° C.), 0.1 % Triton X-100, 1.5 mM MgCl2, and either 200 or 100 µM $MnCl_2$ in a volume of 25 µl and were run for 30 cycles at 95° C. for 1 min, 52° C. for 1 min, and 75° C. for 1.5 min. PCR products were cut with NcoI and PstI at 37° C. for 45 min. The cleaved products were isolated from a 0.5% agarose gel in 1×TAE buffer by using a Qiagen (Chatsworth, Calif.) gel purification kit. Purified products were ligated into the NcoI and PstI sites of pBAD24 [Guzman, et al. (1995) J. Bacteriol. 177:4121–4130]. These ligation reactions were used as the source of transposase mutants in the papillation assay.

Example 4

Papillation Assay

A papillation assay to detect mutants of Himar1 was performed by transforming 1 µl of a ligation of mutated Himar1 coding sequences in pBAD24 into electrocompetent DL1 cells (see FIG. 2A). Screens of similar design have been used for bacterial transposons, including in Tn5 and Tn10 transposases [Huisman and Kleckner, (1987) Genetics 116:185–189; Krebs and Reznikoff, (1988) Gene 63:277–285; Reznikoff, et al. (1993) Methods Enzymol 217:312–322 ]. Cells also were transformed with pBAD-Marl as a wild-type control. Transformed cells were resuspended in 1 ml of cold LB medium and were shaken at 37° C. for 1 h. Dilutions of these cells were plated onto thick (50 ml in 100-×15-mm dishes) MacConkey lactose agar plates containing Amp and Tet so that there were ≈100–150 colonies per plate, and the plates were incubated at 32° C. for 2–3 days. Typically, papillae could be detected by using the wild-type transposase source at ≈50 h after plating. Potential hypertransposers were picked and grown overnight in LB with Amp, and the mutant transposase source DNA was purified. Putative hypertransposers were examined again by using the papillation assay to confirm hyperactivity.

Example 5

Mating-Out Assay

A mating-out assay, which measures the frequency of transposition of a KanR Himar1 minitransposon from a plasmid to an F factor, was carried out to quantify the activity of the putative hyperactive mutants (see FIG. 2B). RZ212(MK) cells were transformed with individual mutant transpose sources isolated in the papillation assay, and the cells were grown as above. Cells were plated on LB agar containing Amp, Gen, and Cam and were grown overnight at 37° C. Five colonies were picked the following day and were grown for 16 h in LB containing Amp, Gen, and Kan at 37° C. These cells were mated to RZ221 cells by mixing 10 µl of recipient cells from overnight cultures in 1 ml of LB medium. The mating mixture was shaken gently at 37° C. for 6–10 h. Mating cultures were vortexed vigorously, and suitable dilutions were plated on LB agar plates containing Nal and Gen to detect total numbers of exconjugates and Nal and Kan to measure the number of exconjugates that contained a Himar1 insertion.

Example 6
Transposase Purification

Transposases were purified as described in Lampe, et al. (1996) supra. Protein purity was determined by Coomassie blue-stained 10–20% polyacrylamide gradient gels. Protein concentrations were determined spectrophotometrically as described in Lampe, et al. (1998) supra and were confirmed visually on Coomassie blue-stained 4–20% SDS/PAGE gels.

Example 7
In Vitro Transposition Assay

Comparative rates of transposition were determined by measuring the relative ability of the transposases to incorporate a radiolabeled DNA fragment containing the left ITR of Himar1 into an unlabeled supercoiled plasmid target in a reaction similar to that for Tn10 in vitro (FIG. 4) [Kennedy and Haniford, D. B. (1996) *J. Mol. Biol.* 256:533–547]. The fragment containing the ITR was labeled by cutting p27fH5' [Lampe, et al. (1996) supra] with EcoRI and isolating the 111-bp fragment on a 1.5%, 1×TAE agarose gel. The DNA was purified from the agarose as described above and then was radiolabeled by filling the overhanging ends with $^{32}$P-α-dATP using Klenow enzyme under standard conditions. The reaction was stopped by heating to 70° C. for 20 min, and the labeled DNA was purified by passing the reaction over a G50 spin column.

Transposition reactions contained 10% glycerol (vol/vol), 25 mM Hepes (pH 7.9 at room temperature), 250 μg acetylated BSA, 2 mM DTT, 100 mM NaCl, 5 mM $MgCl_2$, 450 ng of target plasmid DNA, ≈10,000 cpm labeled ITR DNA, and a 10 nM concentration of one of the purified transposases. Reactions were performed at 28° C., the optimal temperature for wild-type Himar1 transposase [Lampe, et al. (1998) supra]. Ten-microliter aliquots were removed at 1-h intervals of 6 h, and the reaction was stopped by adding 2 μl of stop solution (60 mM EDTA/0.25% bromophenol blue/0.25% xylene cyanol/15% ficoll). Reaction products were separated on a 0.5 % 1×TE agarose gel. The gel was photographed, was placed on a piece of exposed x-ray film as a support, and then was dried until completely flat in a forced-air oven set at 55 ° C. for 5–6 h. Reaction products in dried gels were analyzed by using a Molecular Dynamics PhosphorImager (Molecular Dynamics, Sunnyvale, Calif.) and IMAGEQUANT software (Molecular Dynamics, Sunnyvale, Calif.).

Example 8
Mutagenesis of *Haemophilus influenzae*

In vitro reactions for *H. influenzae* mutagenesis were conducted as above except that 100 nM transposase was added to reactions containing 500 ng of target PCR product and 200 ng of transposon donor plasmid pENT3 carrying Tn-magellan1. Independent reactions and transformations were performed in triplicate. Repair of transposon junctions and transformation of *H. influenzae* was as described [Akerley, et al. (1998) *Proc. Natl. Acad. Sci. USA.* 95:8927–8932].

Example 9
Genetic Assay for in vitro Transposition

In vitro transposition assays were carried out in 10% glycerol (v/v), 25 mM HEPES (pH 7.9 at room temperature), 250 μg of acetylated bovine serum albumin (BSA). 2 mM DDT, 100 mM NaCl and 5 mM $MgCl_2$, and contained ~12.5 nM purified transposase in a final volume of 20 μl. The donor plasmid was pMarKan described in Lampe, et al. (1996) supra. The target plasmid was a naturally occurring tetramer of pBSKS+. Approximately 12 fmol (~100 ng) of target DNA and 12 fmol of donor DNA (~32 ng) were used per each 20 μl reaction. The reactions wee allowed to incubate for 2 h at room temperature. They were then stopped by the addition of 80 μl of stop solution (50 mM Tris-HCl, pH 7.6; 0.5 mg/ml proteinase K: 10 mM EDTA; 250 μg/ml yeast tRNA), and allowed to incubate at 37° C. for 30 min after which they were phenol/chloroform extracted and precipitated using standard techniques. The precipitated DNA was resuspended in 10 μl of TE and 1 μl was electrotransformed into TOP10F' *E. Coli* cells (Invitrogen) using a BRL electroporation device following the manufacturer's instructions. One ml of SOC (0.5% yeast extract, 2% tryptone, 10 mM NaCl, 2.5 mM KCl, 10 mM $MgCl_2$, 20 mM $MgSO_4$, 20 mM glucose) was added to the transformed cells and the suspension incubated at 37° C. with vigorous shaking for 45 min. One μl of the cells was plated on LB-ampicillin (100 μg/ml) agar plates to test for DNA recovery and 500 μl were plated on LB-ampicillin (100 μg/ml)-kanamycin (30 μg/ml) agar plates to detect transposition products. DNA from potential transposition products was prepared by a boiling miniprep method (Sambrook, et al. 1989) and examined by restriction digestion and sequencing. Reactions containing $Mn^{2+}$ were performed identically except 5 mM $MnCl_2$ was substituted for $MgCl_2$ in the in vitro assay. Controls were performed by adding a mock transposase extract in place of purified transposase. This extract was made from uninduced *E. Coli* cells carrying the pET 13a/mariner construct in a manner identical to that of induced cells.

Figure 6A:
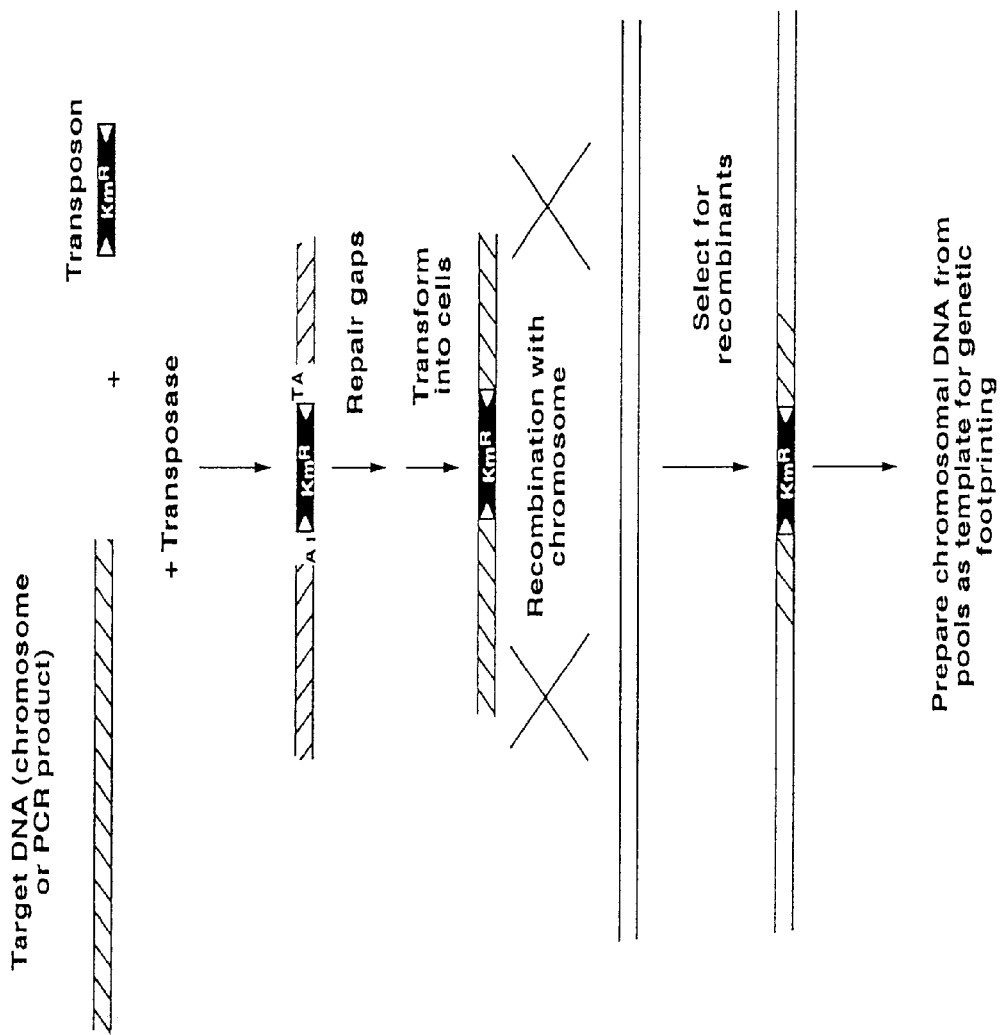
FIGS. 6A and 6B show the GAMBIT method to identify essential genes. A critical part of this methodology utilizes in vitro Himar1 transposition.
Figure 6B:
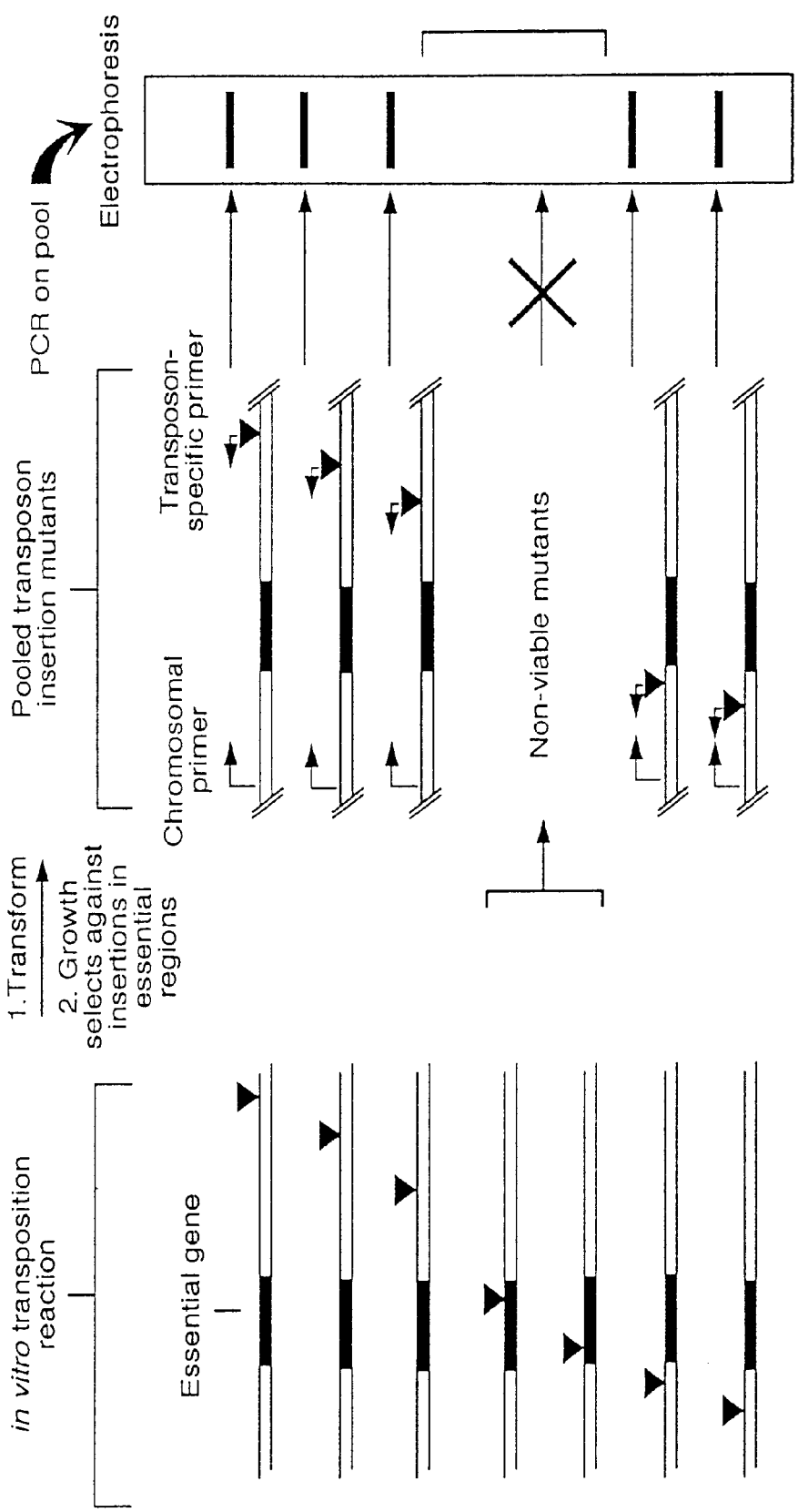

Example 10
Identification of Essential Genes Using the Himar1 Mutant Transposase The details of this method is provided in Akerley, et al. (1998) *Proc. Natl. Acad. Sci. USA* 95:8927–8932 and Akerley, et al. WO 99/50402. As illustrated in FIG. 6, target DNA is mutagenized in vitro with the modified Himar1 transposon containing one of the mutant transposases disclosed herein and introduced into bacteria by transformation and homologous recombination. Recombinants were selected for drug resistance encoded by the transposon, and insertions in essential genes were lost from the pool during growth. PCR with primers that hybridize to the transposon and to specific chromosomal sites yields a product corresponding to each mutation in the pool. DNA regions containing no insertions yield a blank region on the electrophoresis gels.

What is claimed is:

1. A mutant Himar1 transposase having a higher transposition activity than wild type Himar1 transposase wherein said mutant transposase comprises the amino acid sequence selected from the group consisting of the sequences as set forth in SEQ ID Nos: 4, 6, 8, 10, 12, and 14.

2. The mutant transposase of claim 1 comprising the amino acid sequence as set forth in SEQ ID NO:6.

3. The mutant transposase of claim 1 comprising the amino acid sequence as set forth in SEQ ID NO:10.

4. The mutant transposase of claim 2 wherein the transposase is encoded by the nucleotide sequence as given in SEQ ID NO:5.

5. The mutant transposase of claim 3 wherein the transposase is encoded by the nucleotide sequence as given in SEQ ID NO:9.

6. A modified Himar1 transposon comprising a nucleotide sequence encoding a mutant transposase selected from the group consisting of the proteins having the amino acid sequences as set forth in SEQ ID NOs: 4, 6, 8, 10, 12, and 14.

7. The modified Himar1 transposon of claim 6 wherein the nucleotide sequence encodes the mutant transposase consisting of the amino acid sequence as shown in SEQ ID NO:6.

8. The modified Himar1 transposon of claim 6 wherein the nucleotide sequence encodes the mutant transposase consisting of the amino acid sequence as shown in SEQ ID NO:10.

9. The modified Himar1 transposon of claim 7 wherein said nucleotide sequence consists of sequences as shown in SEQ ID NO:5.

10. The modified Himar1 transposon of claim 8 wherein said nucleotide sequence consists of sequences as shown in SEQ ID NO:9.

11. A method of recombinantly producing mutant Himar1 transposase protein in a host cell, said method comprising the steps of:
   a) transformimg a host cell which expresses mutant Himar1 transposase coding sequence with a vector comprising a promoter active in said host cell operably linked to a coding region for said transposase polypeptide comprising an amino acid sequence as set forth in SEQ ID NO:4; SEQ ID NO:6; SEQ ID NO:8; SEQ ID NO:10; SEQ ID NO:12; SEQ ID NO:14, to produce a recombinant host cell; and
   b) culturing the recombinant host cell under conditions wherein said mutant transposase protein is expressed.

12. The method of claim 11 wherein said host cell is selected from the group consisting of bacterial cells, yeast cells, insect cells, and mammalian cells.

13. The method of claim 12 wherein said host cell is *E. Coli*.

14. An expression vector comprising a nucleic acid encoding a mutant Himar1 transposase protein consisting of the amino acid sequence as set forth in SEQ ID NO:6.

15. An expression vector comprising a nucleic acid encoding the mutant Himar1 transposase protein consisting of the amino acid sequence as set forth in SEQ ID NO:10.

16. A recombinant host cell transformed to contain the expression vector of claim 14.

17. A recombinant host cell transformed to contain the expression vector of claim 15.

18. A method for in vitro transposition, the method comprising the steps of:
   combining a donor DNA molecule comprising a transposable DNA sequence of interest with a target DNA molecule and a mutant Himar1 transposase o f claim 1 under conditions such that the mutant Himar1 transposase mediates transposition of the DNA sequence of interest to the target DNA.

19. The method of claim 18 wherein the mutant transposase consists of the amino acid sequence as given in SEQ ID NO:6.

20. The method of claim 18 wherein the mutant transposase consists of the amino acid sequence as given in SEQ ID NO:10.

21. The method of claim 18 wherein said DNA sequence of interest comprises a primer sequence for DNA sequencing.

22. A method for in vivo transposition, the method comprising the steps of:
   introducing a donor DNA molecule comprising a transposable DNA sequence of interest and a modified Himar1 transposon comprising a mutant Himar1 transposase of claim 1 into an organism, cell or tissue under conditions such that the mutant transposase mediates transposition of the DNA sequence of interest to the chromosome of the organism or cell or tissue.

23. The method of claim 22, wherein the mutant Himar1 transposase consist of the amino acid sequence as given in SEQ ID NO:6.

24. The method of claim 22, wherein the mutant Himar1 transposase consists of the amino acid sequence as given SEQ ID NO:10.

* * * * *